United States Patent
Sherwood et al.

(10) Patent No.: US 7,179,488 B2
(45) Date of Patent: *Feb. 20, 2007

(54) PROCESS FOR CO-SPRAY DRYING LIQUID HERBAL EXTRACTS WITH DRY SILICIFIED MCC

(76) Inventors: Bob Sherwood, Route 44, Box 364, Amenia, NY (US) 12501; Joseph A. Zeleznik, 99 E. Cedar St., Poughkeepsie, NY (US) 12601; David Schaible, 501 Popletown Rd., Ulster Park, NY (US) 12487; Wilhelm Berkulin, Schulstrasse 21, D-56237 Alsbach (DE); Karl-Hans Theissing, Kreuzgasse, D-63755 Alzenau-Hörstein (DE)

( * ) Notice: Subject to any disclaimer, the term of this patent is extended or adjusted under 35 U.S.C. 154(b) by 426 days.

This patent is subject to a terminal disclaimer.

(21) Appl. No.: 10/256,855

(22) Filed: Sep. 27, 2002

(65) Prior Publication Data

US 2003/0203050 A1 Oct. 30, 2003

Related U.S. Application Data

(60) Provisional application No. 60/334,443, filed on Nov. 30, 2001, provisional application No. 60/334,398, filed on Nov. 29, 2001.

(51) Int. Cl.
*A61K 9/14* (2006.01)
*A61K 36/00* (2006.01)
(52) U.S. Cl. .................. 424/489; 424/725; 424/195.15
(58) Field of Classification Search ........ 424/725–779, 424/195.15, 489, 496
See application file for complete search history.

(56) References Cited

U.S. PATENT DOCUMENTS

| | | | |
|---|---|---|---|
| 2,756,177 A | 7/1956 | Cannalonga | 167/81 |
| 4,395,491 A | 7/1983 | Höhl et al. | 435/262 |
| 4,519,961 A | 5/1985 | Schumacher et al. | 264/4.6 |
| 4,533,674 A | 8/1985 | Schmidt et al. | |
| 5,466,452 A | 11/1995 | Whittle | |
| 5,585,115 A | 12/1996 | Sherwood et al. | 424/489 |
| 5,709,880 A | 1/1998 | Del Corral et al. | |
| 5,725,883 A | 3/1998 | Staniforth et al. | 424/489 |
| 5,725,884 A | 3/1998 | Sherwood et al. | 424/489 |
| 5,733,578 A | 3/1998 | Hunter et al. | 424/489 |
| 5,741,524 A | 4/1998 | Staniforth et al. | 424/489 |
| 5,798,101 A | 8/1998 | Haveson | |
| 5,858,412 A | 1/1999 | Staniforth et al. | 424/489 |
| 5,866,166 A | 2/1999 | Staniforth et al. | 424/489 |
| 5,965,166 A | 10/1999 | Hunter et al. | 424/489 |
| 6,030,645 A | 2/2000 | Tritsch et al. | 424/490 |
| 6,103,219 A | 8/2000 | Sherwood et al. | 424/494 |
| 6,106,865 A | 8/2000 | Staniforth et al. | 424/489 |
| 6,117,451 A | 9/2000 | Kumar | 424/465 |
| 6,153,220 A | 11/2000 | Cummings et al. | |
| 6,190,696 B1 | 2/2001 | Groenewoud | |
| 6,217,907 B1 | 4/2001 | Hunter et al. | 424/489 |
| 6,217,909 B1 | 4/2001 | Sherwood et al. | 424/494 |
| 6,358,533 B2 | 3/2002 | Sherwood et al. | 424/494 |
| 6,383,526 B1 * | 5/2002 | Andrews et al. | 424/733 |
| 6,391,337 B2 | 5/2002 | Hunter et al. | 424/474 |
| 6,395,303 B1 | 5/2002 | Staniforth et al. | 424/499 |
| 6,447,815 B1 | 9/2002 | Menon et al. | 424/737 |
| 6,471,994 B1 * | 10/2002 | Staniforth et al. | 424/489 |
| 6,521,261 B2 | 2/2003 | Sherwood et al. | 424/494 |
| 6,872,336 B2 | 3/2005 | Tanno et al. | 264/7 |

FOREIGN PATENT DOCUMENTS

| | | |
|---|---|---|
| DE | 0248917 | 8/1987 |
| EP | 0419308 | 3/1991 |
| EP | 1297825 | 9/2002 |
| GB | 0417552 | 10/1934 |
| GB | 1098065 | 1/1968 |
| WO | WO/15155 A1 | 4/1999 |
| WO | 0174448 | 10/2001 |
| WO | 0241838 | 5/2002 |

OTHER PUBLICATIONS

Supplementary Search Report for EP Application No. 01274927.1.
"Drying Plant Extracts—by Adding Polysaccharide, Protein or Resin to Extract Before Spray Drying" DERWENT, Apr. 1986, XP002194486 *Abstract*.

* cited by examiner

Primary Examiner—Christopher R. Tate

(57) ABSTRACT

A process for preparing dry extracts from a liquid extract and at least one additional substance by a spray-drying process, characterized in that said at least one additional substance is added to the spray-drying process in a dry form during the spray-drying processes.

13 Claims, 13 Drawing Sheets

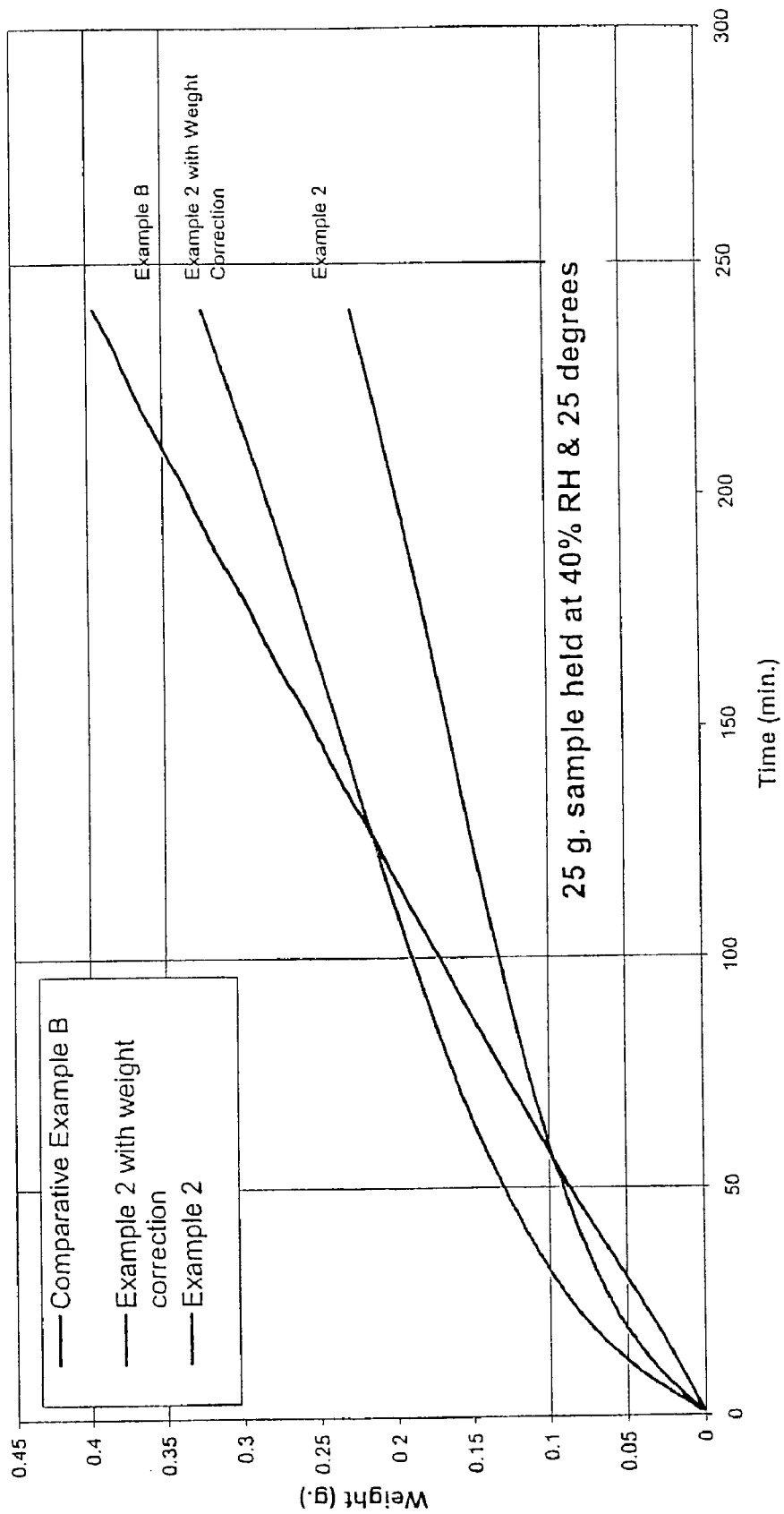
Figure 8: Moisture Uptake of Ginseng Extracts

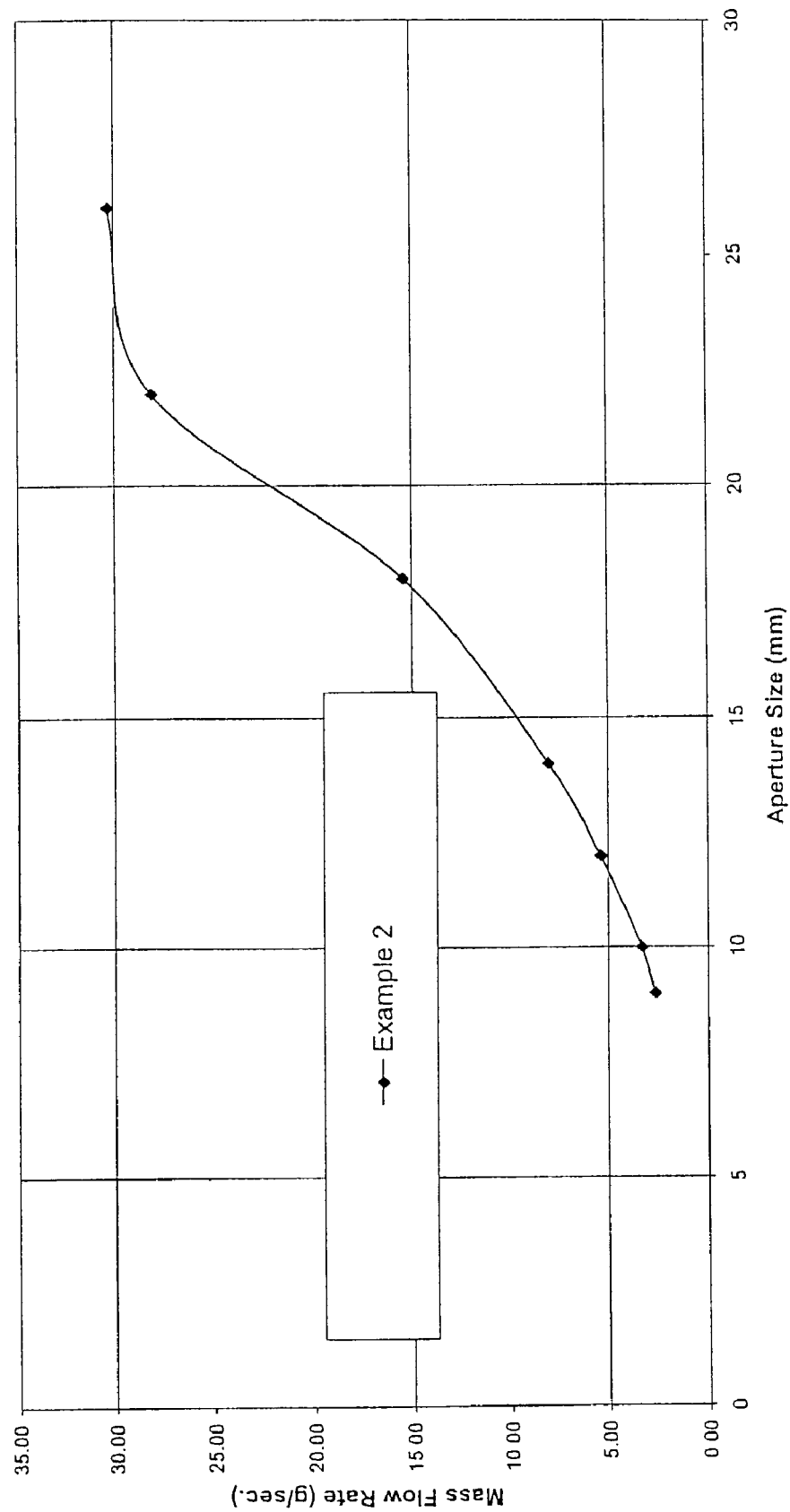
Figure 9: Mass Flow of Ginseng Extract

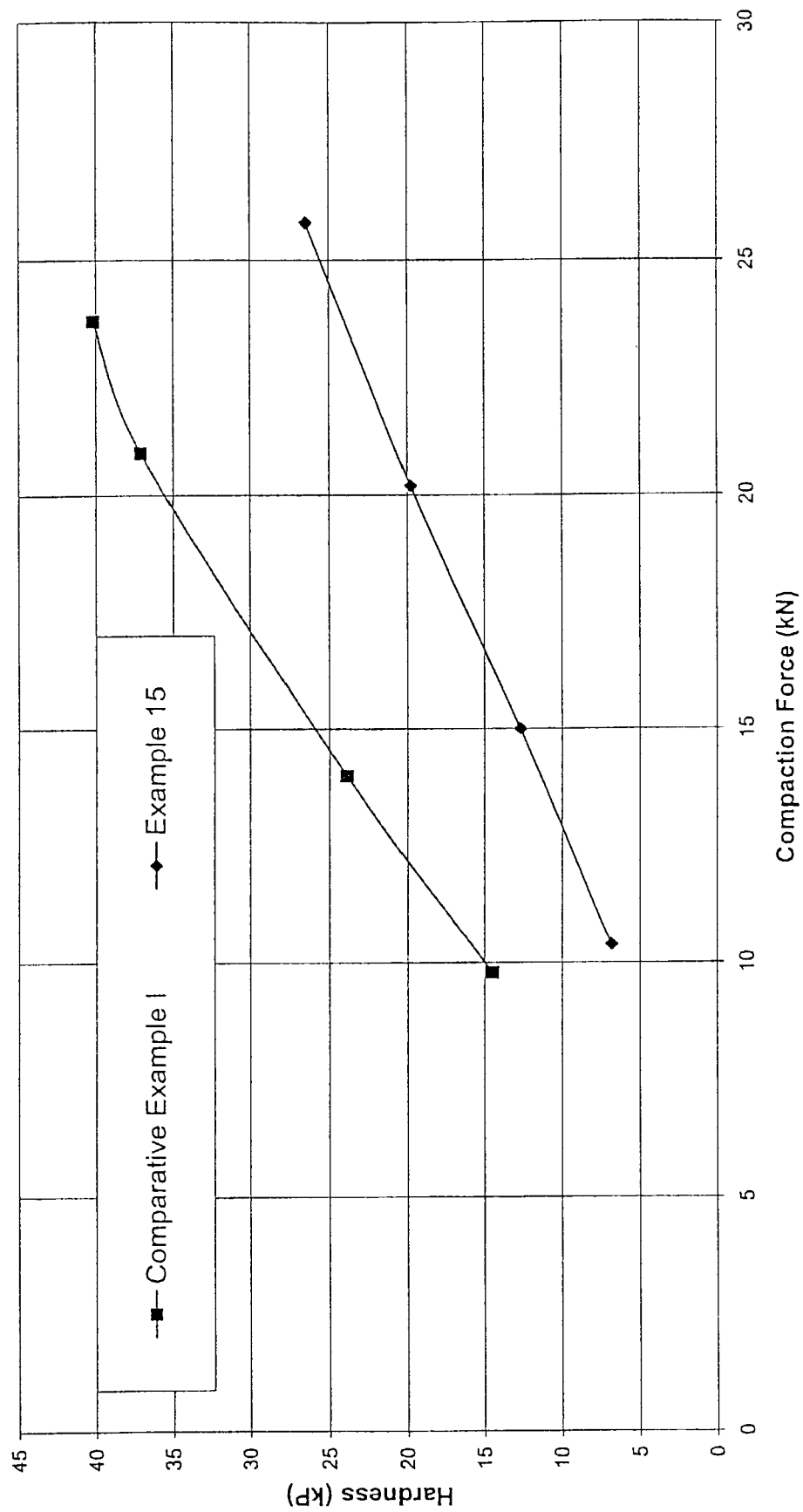

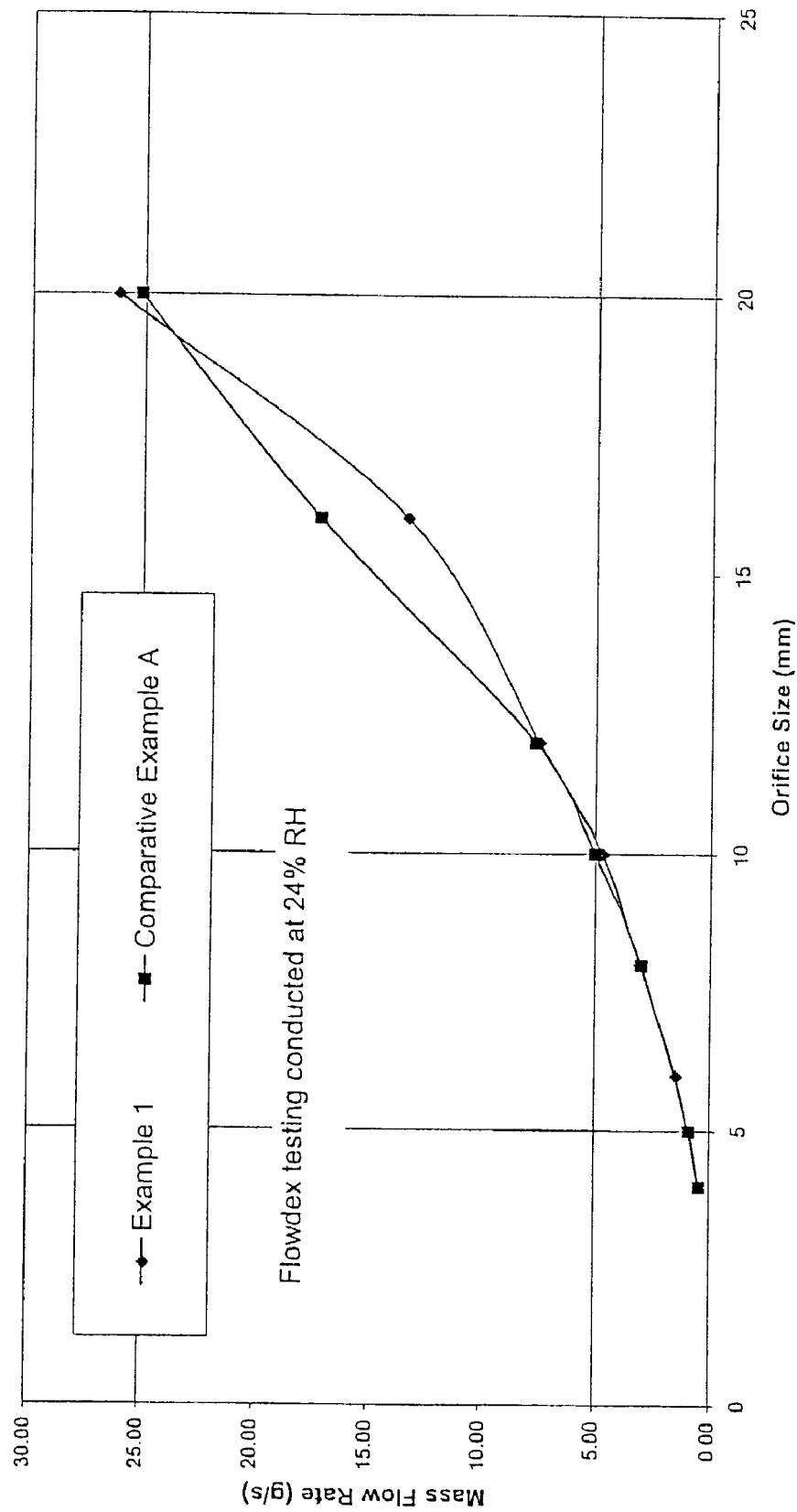

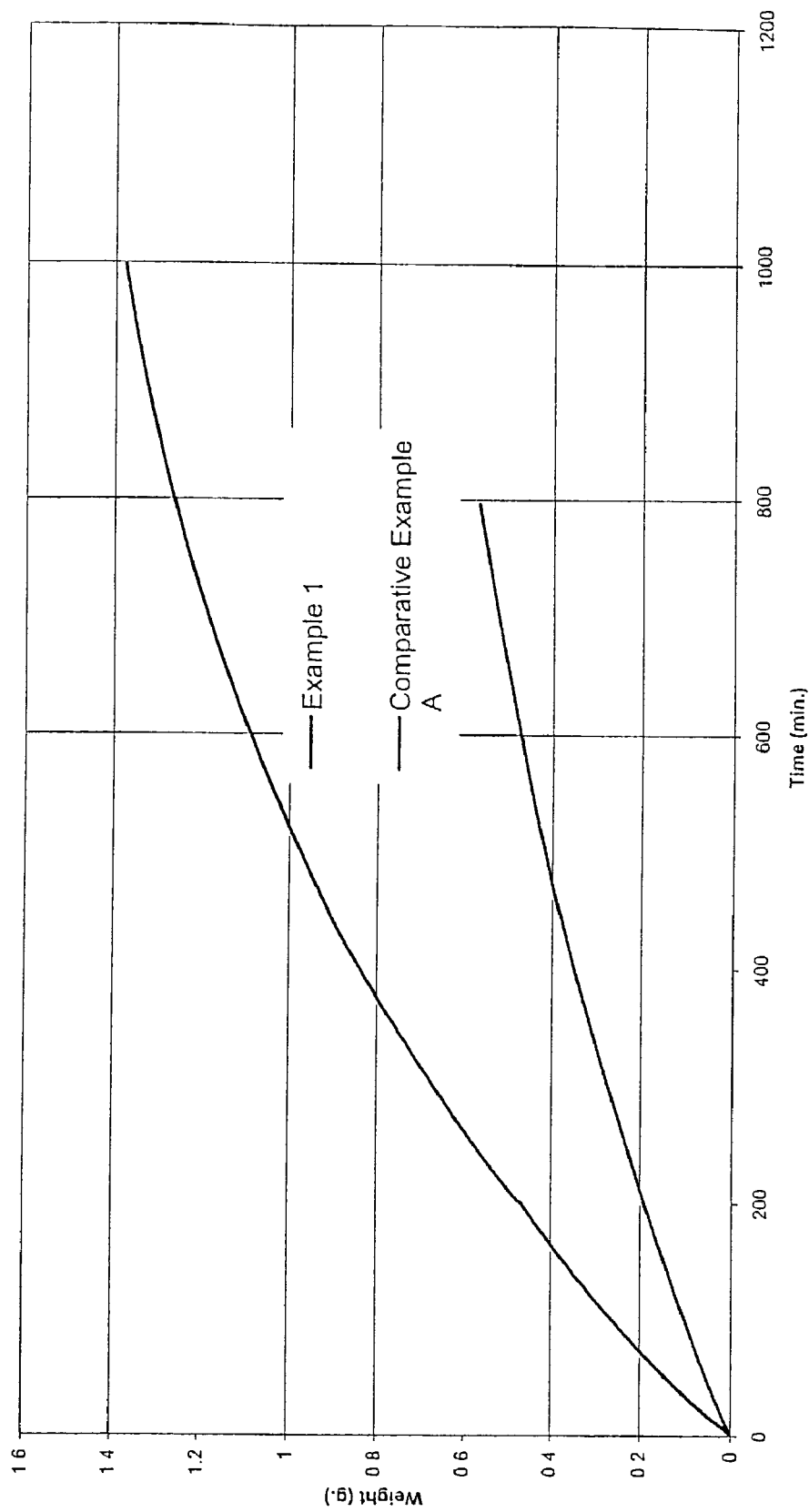
Figure 12: Moisture Uptake of Artichoke Extract

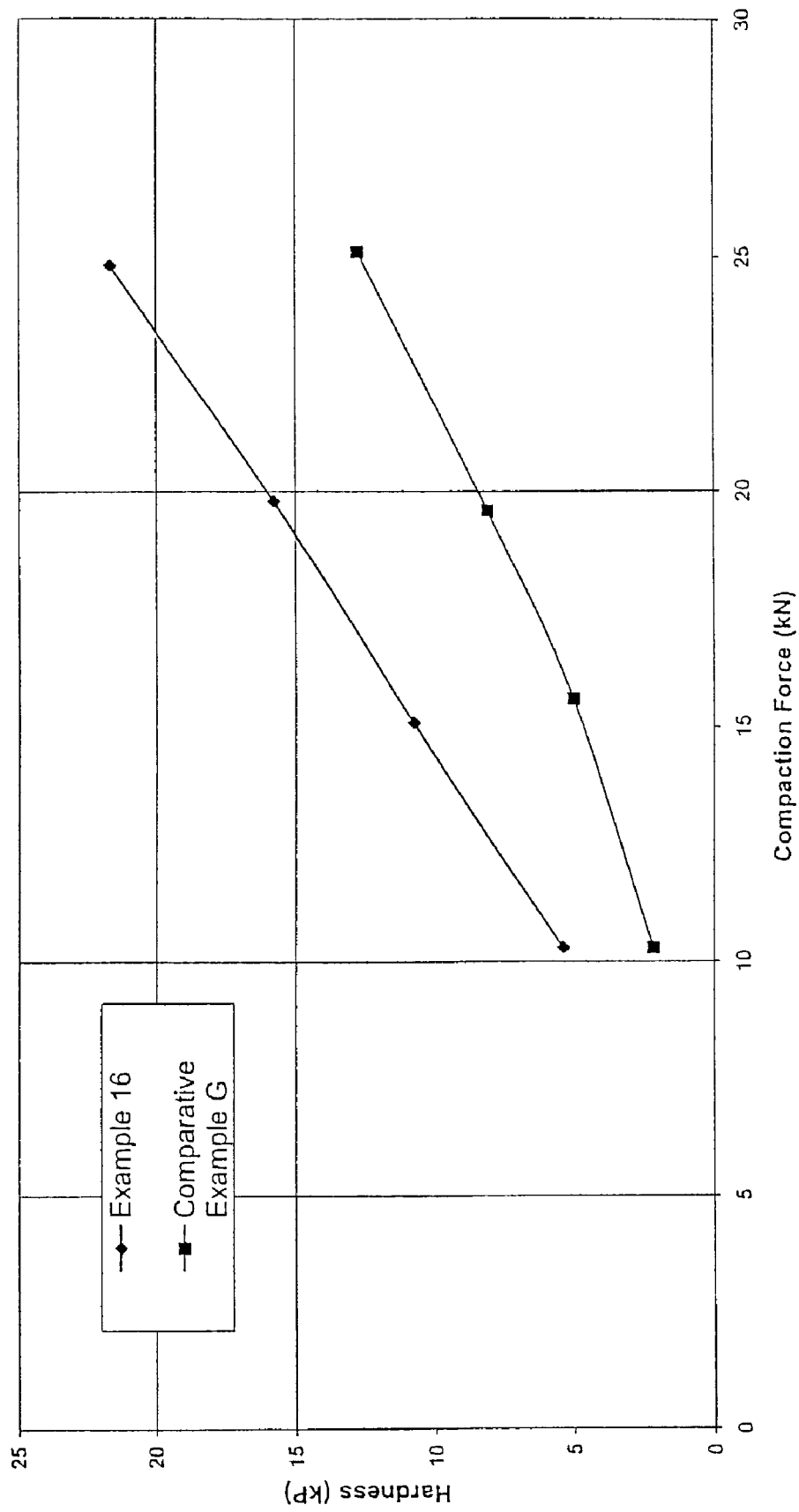

ial and nutriceutical active agents and excipients. In
PROCESS FOR CO-SPRAY DRYING LIQUID HERBAL EXTRACTS WITH DRY SILICIFIED MCC This application claims priority from U.S. Provisional Application Ser. Nos. 60/334,443 and 60/334,398, filed Nov. 30, 2001 and Nov. 29, 2001, respectively, the entire disclosures of which are hereby incorporated by reference.

BACKGROUND

Spray dryers are well known in the art for drying pharmaceutical and nutriceutical active agents and excipients. In general, a spray dryer is used to process fluid materials into powders. Typically, the fluid material is introduced into the spray dryer in the form of a solution, suspension, emulsion, slurry, or thin paste. In operation, the fluid material is fed from a feed delivery system to an atomizer. The atomizer disperses the fluid material into the drying chamber in fine droplets. A heated air supply applies heated air to the fine droplets in the drying chamber, causing the fine droplets to be dried into a powder, the powder being collected in a collection system. Spray dryers are widely used in the preparation of active agents. For example, it is known to spray dry an active agent in the form of a fluid material (for example, a liquid herbal extract) to form a powder, and thereafter, to blend the powder with conventional tableting agents, and then compress the resulting mixture into a tablet.

Examples of such tableting agents include lubricants, diluents, binders, disintegrants, and direct compression vehicles. Lubricants are typically added to avoid the material(s) being tableted from sticking to the punches. Commonly used lubricants include magnesium stearate, stearic acid, sodium stearyl fumarate, hydrogenated vegatable oil, and calcium stearate. Such lubricants are commonly included in the final tableted product in amounts of less than 1% by weight. Diluents are frequently added in order to increase the bulk weight of the material to be tableted in order to make the tablet a practical size for compression. This is often necessary where the dose of the drug is relatively small. Binders are agents which impart cohesive qualities to the powdered material(s). Commonly used binders include starch, and sugars such as sucrose, glucose, dextrose, and lactose. Typical disintegrants include starch derivatives and salts of carboxymethylcellulose. Direct compression vehicles include, for example, processed forms of cellulose, sugars, and dicalcium phosphate dihydrate, among others. Microcrystalline cellulose is an example of a processed cellulose that has been utilized extensively in the pharmaceutical industry as a direct compression vehicle for solid dosage forms.

Silicified microcrystalline cellulose is a particularly useful direct compression vehicle. Silicified microcrystalline cellulose is a particulate agglomerate of coprocessed microcrystalline cellulose and from about 0.1% to about 20% silicon dioxide, by weight of the microcrystalline cellulose, the microcrystalline cellulose and silicon dioxide being in intimate association with each other, and the silicon dioxide portion of the agglomerate being derived from a silicon dioxide having a particle size from about 1 nanometer (nm) to about 100 microns (μm), based on average primary particle size. Preferably, the silicon dioxide comprises from about 0.5% to about 10% of the silicified microcrystalline cellulose, and most preferably from about 1.25% to about 5% by weight relative to the microcrystalline cellulose. Moreover, the silicon dioxide preferably has a particle size from about 5 nm to about 40 μm, and most preferably from about 5 nm to about 50 μm. Moreover, the silicon dioxide preferably has a surface area from about 10 $m^2$ g to about 500 $m^2$/g, preferably from about 50 $m^2$/g to about 500 $m^2$/g, and more preferably from about 175 $m^2$/g to about 350 $m^2$/g. Silicified microcrystalline cellulose, and methods for its manufacture, are described in U.S. Pat. No. 5,585,115, the entire disclosure of which is hereby incorporated by reference. Silificified microcrystalline cellulose is commercially available from Penwest Pharmaceuticals, Inc., under the trademark Prosolv®. Prosolv is available in a number of grades, including, for example, Prosolv SMCC 50, Prosolv SMCC 90, and Prosolv HD.

SUMMARY OF THE INVENTION

In accordance with one embodiment of the present invention, a solid dosage form is provided which includes an active agent and silicified microcrystalline cellulose, the dosage form being formed by a) combining a wetted active agent with dry silicified microcrystalline cellulose in a dryer to form agglomerated particles; and b) incorporating the agglomerated particles into the solid dosage form. In certain preferred embodiments, step b) comprises co-drying said silicified microcrystalline cellulose, said active agent, and colloidal silicon dioxide in a dryer. Preferably, the dryer is a spray dryer, and, in certain embodiments, the active agent may be an herbal extract.

In accordance with another embodiment of the present invention, a solid dosage form is provided which includes an active agent and silicified microcrystalline cellulose, the dosage form being formed by a) providing an active agent suitable for spray drying; b) combining the active agent and silicified microcrystalline cellulose in a spray dryer to form agglomerated particles; and c) incorporating the agglomerated particles into a solid dosage form. In accordance with further aspects of this embodiment, the silicified microcrystalline cellulose may be in a slurry, suspension, solution, or emulsion (with or without the active agent) prior to being combined with the active agent in the dryer. Alternatively, the silicified microcrystalline cellulose may be introduced into the dryer in dry form In accordance with another embodiment of the present invention, a method of manufacturing a tablet containing an herbal extract is provided which comprises: a) providing an extract composition comprising an herbal extract suitable for spray drying; b) combining the herbal extract with a dry silicified microcrystalline cellulose in a dryer to form agglomerated particles; and c) compressing the agglomerated particles into tablets.

In accordance with another embodiment of the present invention, an oral solid dosage form is provided which comprises at least about 60% ginseng extract and from about 25 to about 40%, silicified microcrystalline cellulose. In accordance with another embodiment of the present invention, a tablet is provided which comprises at least about 60% St John's Wort extract and from about 25 to about 40% silicified microcrystalline cellulose. In accordance with another embodiment of the present invention, a tablet is provided which comprises at least about 60% artichoke leaves extract and from about 25 to about 40% silicifled microcrystalline cellulose.

In accordance with yet another embodiment of the present invention, agglomerated particles of an active agent and silicified microcrystalline cellulose are provided, the agglomerated particles being formed by combining the active agent and dry silicified microcrystalline cellulose in a dryer to form agglomerated particles, the agglomerated particles having an average particle size of from about 10 μm to about 500 μm. Preferably, the agglomerated particles having an average particle size of from about 15 μm to about 300 μm.

In accordance with still another embodiment of the present invention, a tablet is provided that comprises an herbal extract and augmented microcrystalline cellulose prepared by spray drying a wetted herbal extract with dry agglomerated particles comprised of microcrystalline cellulose and a compressibility augmenting agent selected from the group consisting of pharmaceutically acceptable colloidal metal oxides and colloidal carbon black. In certain embodiments, the colloidal metal oxide may be colloidal titanium dioxide.

In accordance with another embodiment of the present invention, a process for preparing dry extracts from a liquid extract and at least one additional substance by a spray-drying process is characterized in that said at least one additional substance is added to the spray-drying process in a dry form during the spray-drying processes.

As described in further detail below, the agglomerated particles in accordance with certain embodiments of the present invention described above provide a number of advantages including superior flow characteristics and superior compaction characteristics to prior art compositions. As one of ordinary skill in the art will appreciate, the superior compaction characteristics provided by these embodiments of the present invention allow faster and more efficient processing for tablets, and, moreover, allow a larger percentage of active agent to be included in each tablet.

The term "environmental fluid" is meant for purposes of the invention to encompass, e.g., an aqueous solution, or gastrointestinal fluid.

By "sustained release" it is meant for purposes of the invention that a therapeutically active medicament is released from the formulation at a controlled rate such that therapeutically beneficial blood levels (but below toxic levels) of the medicament are maintained over an extended period of time, e.g., providing a 12 hour or a 24 hour dosage form.

By "primary particle size" it is meant for purposes of the invention that the particles are not agglomerated. Agglomeration is common with respect to silicon dioxide particles, resulting in a comparatively average large agglomerated particle size.

By fluid (or liquid) material, it is meant for purposes of the invention that the material (e.g., the active agent) is sufficiently wetted to be suitable for subsequent spray drying.

BRIEF DESCRIPTION OF THE DRAWINGS

FIG. 8 is a graph of moisture uptake for the Ginseng extract compositions of Examples 2 and B.

FIG. 9 is a graph of mass flow (g/s) as a function of aperture size (mm) for the Ginseng composition of Example 2.

FIG. 10 is a graph of tablet hardness as a function of compaction force for the compositions of Examples I and 15.

FIG. 11 is a graph of mass flow (g/s) as a function of aperture size (mm) for the artichoke extract compositions of Examples 1 and A.

FIG. 12 is a graph of moisture uptake for artichoke extract compositions of Examples 1 and A.

FIG. 13 is a graph of tablet hardness as a function of compaction force for the compositions of Examples 16 and G.

DETAILED DESCRIPTION OF THE PREFERRED EMBODIMENTS

Figure 1:
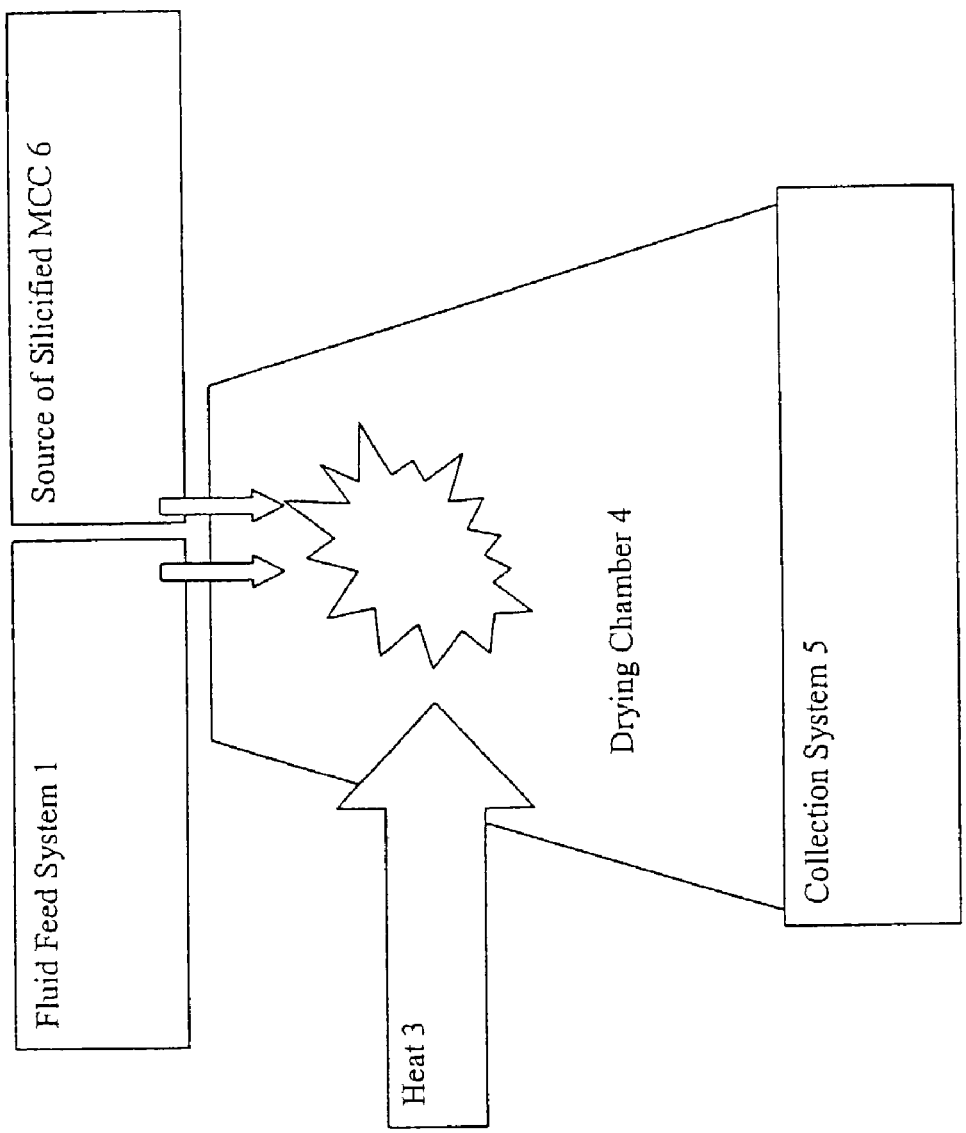
FIG. 1 is a block diagram of a spray dryer including a fluid active agent and a source of silicified microcrystalline cellulose.

Spray dryers are well known in the art for drying pharmaceutical and nutriceutical active agents and excipients. In general, a spray dryer is used to process fluid materials into powders. Typically, the fluid material is introduced into the spray dryer in the form of a solution, slurry, suspension, emulsion, or thin paste. Referring to FIG. 1, a typical spray dryer including a fluid feed system 1, an atomizer 2, a heated air supply 3, a drying chamber 4, and a collection system 5. In operation, the fluid material is fed from the fluid feed system to the atomizer. The atomizer disperses the fluid material into the drying chamber in fine droplets. The heated air supply applies heated air to the fine droplets in the drying chamber, causing the fine droplets to be dried into a powder, the powder being collected in the collection system. In certain spray dryers, extremely fine particles that float up from the collection system (referred to in the art as "fines") are recycled back into the path of the atomized fluid material.

In accordance with an embodiment of the present invention, the fluid material is an active agent, and silicified microcrystalline cellulose from (hereinafter "silicified MCC") from, for example a source of silicified MCC 6, is fed into the drying chamber 4 and is interdispersed with the atomized fluid material as the heat 3 is applied. As the atomized fluid material dries, it is combined with the silicified MCC so that the powder collected in the collection system 5 includes agglomerated particles of active agent/silicified MCC.

As noted above, by fluid (or liquid ) material, it is meant that the material (e.g., the active agent) is sufficiently wetted to be suitable for subsequent spray drying. For example, the material may be in a solution, a suspension, a slurry, or an emulsion. Moreover, the solution may include one or more of a variety of solvents, including water, alcohol, ethanol, and the like. Hydro-alcohol solvents may also be used.

In certain embodiments, dry silicified MCC is fed into the drying chamber. In another embodiment, a slurry of silicified MCC (e.g., a slurry of Prosolv SMCC 90) is formed, and the silicified MCC slurry is fed into the drying chamber as an atomized silicified MCC fluid. In such an embodiment, the silicified MCC slurry can be introduced into the drying chamber separately from the atomized active fluid material (e.g., through a separate spray nozzle), or the silicified MCC can be combined with the active fluid material prior to atomization (e.g., as a slurry in the fluid feed system), and the active fluid material and silicified MCC could be atomized together.

In certain embodiments in which dry silicified MCC is fed into the drying chamber, the dry silicified MCC may be fed into the drying chamber along with the recycled fines.

In any event, the silicified MCC is preferably fed into the drying chamber at a rate sufficient to cause the agglomerated particles to contain at least about 25% silicified MCC, and preferably at least about 30% silicified MCC. Most preferably, the silicified MCC is fed into the drying chamber at a rate sufficient to cause the agglomerated particles to contain from about 30% to about 40% silicified MCC.

In accordance with a further embodiment of the present invention, dry colloidal silicon dioxide is also fed into the drying chamber and is interdispersed with the silicified MCC and the atomized fluid material. Although the use of dry colloidal silicon dioxide is preferred, in other embodiments, the colloidal silicon dioxide may be fed into the drying chamber as an atomized silicon dioxide fluid (e.g., from a slurry). In any event, the resulting agglomerated particles are agglomerated particles of active agent/silicified MCC/colloidal silicon dioxide. Preferably, the silicified MCC and colloidal silicon dioxide is fed into the drying chamber at a rate sufficient to cause the agglomerated particles to contain about 25% silicified MCC and about 5% colloidal silicon dioxide.

In the context of the present invention, silicified MCC is a particulate agglomerate of coprocessed microcrystalline cellulose and from about 0.1% to about 20% silicon dioxide, by weight of the microcrystalline cellulose, the microcrystalline cellulose and silicon dioxide being in intimate association with each other, and the silicon dioxide portion of the agglomerate being derived from a silicon dioxide having a particle size from about 1 nanometer (nm) to about 100 microns (μm), based on average primary particle size. By "intimate association", it is meant that the silicon dioxide has in some manner been integrated with the microcrystalline cellulose particles, e.g., via a partial coating of the microcrystalline particles, as opposed to a chemical interaction of the two ingredients. The term "intimate association" is therefore deemed for purposes of the present description as being synonymous with "integrated" or "united". The coprocessed particles are not necessarily uniform or homogeneous. Rather, under magnification, e.g., scanning electron microscope at 500 times, the silicon dioxide at the preferred percent inclusion appears to be an "edge-coating". Preferably, the silicon dioxide comprises from about 0.5% to about 10% of the silicified MCC, and most preferably from about 1.25% to about 5% by weight relative to the microcrystalline cellulose. Moreover, the silicon dioxide preferably has a particle size from about 5 nm to about 40 μm, and most preferably from about 5 nm to about 50 μm. Moreover, the silicon dioxide preferably has a surface area from about 10 $m^2$ g to about 500 $m^2$/g, preferably from about 50 $m^2$/g to about 500 $m^2$/g, and more preferably from about 175 $m^2$/g to about 350 $m^2$/g. Silicified MCC, and methods for its manufacture, are described in U.S. Pat. No. 5,585,115, the entire disclosure of which is hereby incorporated by reference. Silificified microcrystalline cellulose is commercially available from Penwest Pharmaceuticals, Inc., under the trademark Prosolv®. Prosolv is available in a number of grades, including, for example, Prosolv SMCC 50, Prosolv SMCC 90, and Prosolv HD, each of which contains 2% colloidal silicon dioxide, by weight relative to the microcrystalline cellulose.

Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil); E. I. DuPont & Co.; and W. R. Grace & Co. Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

The surface area of the preferred class of silicon dioxides utilized in the invention ranges from about 50 $m^2$/gm to about 500 $m^2$/gm. The average primary particle diameter of the preferred class of silicon dioxides utilized in the invention ranges from about 5 nm to about 50 nm. However, in commercial colloidal silicon dioxide products, these particles are agglomerated or aggregated to varying extents. The bulk density of the preferred class of silicon dioxides utilized in the invention ranges from about 20 g/l to about 100 g/l.

Commercially available colloidal silicon dioxide products have, for example, a BET surface area ranging from about 50+−15 $m^2$/gm (Aerosil OX50) to about 400+−20 (Cab-O-Sil S-17) or 390+−40 $m^2$/gm (Cab-O-Sil EH-5). Commercially available particle sizes range from a nominal particle diameter of 7 nm (e.g., Cab-O-Sil S-17 or Cab-O-Sil EH-5) to an average primary particle size of 40 nm (Aerosil OX50). The density of these products range from 72.0+−8 g/l (Cab-O-Sil S-17) to 36.8 g/l (e.g., Cab-O-Sil M-5). The pH of the these products at 4% aqueous dispersion ranges from pH 3.5–4.5. These commercially available products are described for exemplification purposes of acceptable properties of the preferred class of silicon dioxides only, and this description is not meant to limit the scope of the invention in any manner whatsoever.

Another type of colloidal silicon dioxide is surface treated silica, including, for example, hydrophobically modified silica and hydrophilically modified silica. An example of a commercially available hydrophobically modified silica that may be used as the colloidal silicon dioxide in the embodiments described herein is AEROSIL® R 972, manufactured by Degussa A G.

The active agent(s) which may be used in accordance with the embodiments described above include systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, plant growth stimulants, and the like.

A wide variety of therapeutically active agents can be used in conjunction with the present invention. The therapeutically active agents (e.g. pharmaceutical agents) include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

A wide variety of locally active agents can be used in conjunction with the embodiments described herein, and include both water soluble and water insoluble agents. The locally active agent(s) is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g., metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. The solid formulations of the invention may also include other locally active agents, such as flavorants and sweeteners. Generally any flavoring or food additive such as those described in Chemicals Used in Food Processing, pub 1274 by the National Academy of Sciences, pages 63–258 may be used. Generally, the final product may include from about 0.1% to about 5% by weight flavorant.

In accordance with one embodiment of the present invention, the active agent is a liquid herbal extract. As noted above, the term "liquid" as used herein means that the herbal extract is sufficiently wetted to be atomized in a spray dryer. Preferably, the herbal extract is selected from the group consisting of: Alfalfa Leaf, Alfalfa Juice, Aloee-emodin, Andrographolide, Angelica Root, Astragalus Root, Bilberry, Black Cohosh Root, Black Walnut Leaf, Blue Cohosh Root, Burdock Root, Cascara Bark, Cats Claw Bark, Catnip Leaf, Cayenne, Chamomile Flowers, Chaste Tree Berries, Chickweed, Chinese Red Sage Root, Cranberry, Chrysophanol, Comfrey Leaf, Cramp Bark, Damiana Leaf, Dandelion Root CO, Devil's Claw Root, Diosgenin, Dong Quai Root, Dong Quai, Echinacea, Echinacea Angustifolia Root, Echinacea Purpurea Herb Root and Echinacea Angust./Purpurea Blend CO, Echinacea Angust./Goldenseal Blend, Eleuthero (Siberian) Ginseng Root, Emodin, Eyebright Herb, Fenugreek, Feverfew Herb CO, Fo-Ti Root, Fo-Ti, Garcinia Cambogia, Gentian Root, Ginger, Ginko Biloba Ginger Root, Ginseng, Ginko Leaf, Ginseng Root, Goldenseal Root, Gotu Kola Herb, Grape Seed, Grape Skin, Green Tea, Green Tea, Decaf, Guarana Seeds, Gynostemrnma Pentaphyllum, Hawthorn Berries, Hawthorn Leaf, Hesperdin, Hops Flowers, Horehound Herb, Horse Chestnut, Horsetail, Hyssop Leaf, Huperzine A, Juniper Berries, Kava Kava Root, Kola Nut, Lavender Flowers, Lemon Balm, Licorice Root, Lobelia Herb, Lomatium, Marshmallow Root, Milk Thistle Seed, Milk Thistle, Mullein Leaf, Myrrh, Naringin, Neohesperidin, Nettle Leaf, Olive Leaf, Oregon Grape Root, Papain, Parsley Leaf & Root, Passion Flower, Pau D'Arco Bark, Pennyroyal, Peppermint Leaf, Physcion, Polystictus Versicolor Mushroom, Quercetin, Red Clover Blossoms, Red Clover, Red Raspberry Leaf, Red Yeast Rice, Reishi Mushrooms, Rhein, Rhubarb Root, Rosemary Leaf, Rutin, Sarsaparilla Root, Saw Palmetto, Saw Palmetto Berry, Schisandra Berries, Schisandra, Scullcap Herb, Shavegrass Herb, Sheep Sorrel, Shepard's Purse Herb, Shitake Mushroom, Slippery Elm Bark, Sown Orange, Soybean, Stevia Rebaudiana, St. John's Wort, Tetrandrine, Turmeric, Usnea Lichen, Uva Ursi, Uva Ursi Leaf, Valerian Root, White Willow Bark, Wild Yam Root, Yellow Dock Root, Yohimbe Bark, Yucca Root, and combinations thereof. Most preferably, the herbal extract is selected from the group consisting of St. John's Wort, Artichoke Leaves, and Ginseng.

In accordance with certain embodiments of the present invention, the active agent is hygroscopic. Examples of hygroscopic active agents include many herbal extracts, including St. John's Wort, Artichoke Leaves, and Ginseng.

The agglomerated particles in accordance with the embodiments of the present invention described above provide a number of advantages. Specifically, the agglomerated particles provide superior flow characteristics to prior art compositions. As one of ordinary skill in the art will appreciate, the superior flow characteristics provided by the embodiments of the present invention allow faster and more efficient processing for tablets, capsules, and other dosage forms.

The agglomerated particles in accordance with the embodiments of the present invention also provide superior compaction characteristics to prior art compositions. As one of ordinary skill in the art will appreciate, the superior compaction characteristics provided by the embodiments of the present invention allow faster and more efficient processing for tablets, and, moreover, allow a larger percentage of active agent to be included in each tablet. For example, St. John's Wort is currently marketed in 600 mg capsules, wherein each capsule includes 150 mg. of St. John's Wort extract. In contrast, in accordance with certain embodiments of the present invention, 300 mg of St. John's Wort extract can be included in a 450 mg tablet. Similarly, Ginseng is currently marketed in 450 mg tablets, wherein each tablet includes 100 mg. of Ginseng extract. In contrast, in accordance with certain embodiments of the present invention, 500 mg of Ginseng extract can be included in a 752 mg. tablet.

In addition, the agglomerated particles in accordance with the embodiments of the present invention exhibit superior content uniformity when tableted than agglomerated particles that are formed by a wet granulation of silicified MCC and an active agent. This is particularly useful when tableting low dose formulations because such formulations are particularly prone to content uniformity problems. Thus, the agglomerated particles in accordance with the embodiments of the present invention are particularly advantageous with respect to tablets including 100 mg or less active agent in tablets having a total tablet weight between 200 mg and 800 mg. In certain embodiments, the tablets include 50 mg or less active agent in tablets having a total tablet weight of between 200 mg and 800 mg. In other embodiments, the tablets include 10 mg or less active agent in tablets having a total tablet weight of between 50 mg and 800 mg. In still other embodiments, the tablets include 1 mg or less active agent in tablets having a total tablet weight of between 10 mg and 800 mg. In still other embodiments, the tablets include no more than about 20% by weight active agent, preferably no more than about 10% by weight active agent, and most preferably no more than about 1% by weight active agent.

In accordance with other embodiments of the present invention, an augmented microcrystalline cellulose can be substituted for silicified MCC in the above referenced products and processes. In accordance with these embodiments, the augmented microcrystalline cellulose is a particulate agglomerate of coprocessed microcrystalline cellulose and from about 0.1% to about 20% of a compressibility augmenting agent, by weight of the microcrystalline cellulose, the microcrystalline cellulose and compressibility augmenting agent being in intimate association with each other. Examples of suitable compressibility augmenting agents include pharmaceutically (or nutraceutically) acceptable metal oxides such as colloidal titanium dioxide, as well as colloidal carbon black. Surface treated metal oxides may also be used. One skilled in the art will appreciate that other classes of compounds having size, surface area, and other similar physical characteristics to silicon dioxide may also be useful in physically forming a barrier which may reduce the surface-to-surface interactions (including hydrogen-bonding) between cellulose surfaces, and therefore may be used as a compressibility augmenting agent. It should be appreciated that silicified microcrystalline cellulose (which includes the metal oxide silicon dioxide) is also an example of an augmented microcrystalline cellulose as defined herein.

In accordance with still other embodiments of the present invention, pharmaceutically (or nutraceutically) acceptable metal oxides such as colloidal titanium oxide, or colloidal carbon black, can be co-spray dried with the fluid active material and the silicified MCC (or the other compressibility augmenting agents described above).

Although the agglomerated particles in accordance with the embodiments of the present invention described above are preferably manufactured using a spray dryer, it should be appreciated that other types of dryers may alternatively be used, provided that they are capable of forming the agglomerated particles described above.

In accordance with other embodiments of the present invention, the agglomerated particles described above may be combined with conventional tableting additives prior to tableting. For example, if desired, any generally accepted soluble or insoluble inert pharmaceutical filler (diluent) material can be included in the final product (e.g., a solid dosage form). Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, "off-the-shelf" microcrystalline cellulose, mixtures thereof, and the like.

An effective amount of any generally accepted pharmaceutical lubricant, including the calcium or magnesium soaps may optionally be added prior to compression into a solid dosage form. The lubricant may comprise, for example, magnesium stearate in any amount of about 0.5–3% by weight of the solid dosage form.

The complete mixture, in an amount sufficient to make a uniform batch of tablets, may then subjected to tableting in a conventional production scale tableting machine at normal compression pressures for that machine, e.g., about 1500–10,000 lbs/sq in. The mixture should not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally. It is contemplated that for certain uses, e.g., antacid tablets, vaginal tablets and possibly implants, that the tablet will be larger.

In certain embodiments of the invention, the tablet is coated with a sufficient amount of a hydrophobic polymer to render the formulation capable of providing a release of the medicament such that a 12 or 24 hour formulation is obtained. In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100-555.

In further embodiments, the dosage form may be coated with a hydrophilic coating in addition to or instead of the above-mentioned coatings. An example of a suitable material which may be used for such a hydrophilic coating is hydroxypropylmethylcellulose (e.g., Opadry®, commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60°–70° C. for about 3–4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

The coatings which may be optionally applied to the compressed solid dosage form of the invention may comprise from about 0.5% to about 30% by weight of the final solid dosage form.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10 µm if applied via spray-coating or immersion-coating. Generally, in embodiments of the invention wherein a hydrophobic polymer or enteric coating is applied to the tablets, the tablets are coated to a weight gain from about 1% to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, an additional dose of the active agent may be included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of active agent included in the coating layer may be, e.g., from about 10% to about 40% of the total amount of medicament included in the formulation.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857–884, hereby incorporated by reference), stabilizers, binders, odor controlling agents, and preservatives.

Alternatively, the agglomerated particles of active agent/ silicified MCC (with or without silicon dioxide) can be utilized in other applications wherein it is not compressed. For example, the agglomerated particles can be filled into capsules. The agglomerated particles can further be molded into shapes other than those typically associated with tablets. For example, the agglomerated particles can be molded to "fit" into a particular area in an environment of use (e.g., an implant). All such uses would be contemplated by those skilled in the art and are deemed to be encompassed within the scope of the appended claims.

EXAMPLES 1 THROUGH 16 and A THROUGH K

EXAMPLE 1

Agglomerated particles of artichoke leaves extract/Prosolv SMCC 90/silicon dioxide were prepared with the following ingredients:

| Product | Amount/kg |
|---|---|
| Artichoke Leaves Extract: Extr. Cynarae e fol aquos. spiss. (Content of dry substance 70.0%, corresponding to dry substance) | 100.0(70.0) |
| Prosolv SMCC 90 | 30.0 |
| Silicon dioxide, highly dispersed (Aerosil) Ph. Eur. | 5.0 |

The artichoke leaves extract is in the form of a liquid extract (specifically, it is in a water solvent). This liquid extract was placed into the fluid feed system of a spray dryer, atomized, and combined with the Prosolv SMCC 90 and colloidal silicon dioxide in the drying chamber of the spray dryer. In this example, the Prosolv SMCC 90 and colloidal silicon dioxide (both dry) were homogenized (in a mixer), and then fed into the drying chamber along with the recycled fines from the collection system.

The agglomerated particles collected from the collection system provided a yield of 95.2 kg, with the following composition:
   70.0% Artichoke Leaves extract (Extr. Cynarae e fol aquos. spiss)
   25.0% Prosolv (SMCC 90)
   5.0% Silicon dioxide, highly dispersed, Ph. Eur.

COMPARATIVE EXAMPLE A

A mixture of artichoke leaves extract/glucose/maltodextrin/silicon dioxide was prepared with the following ingredients:

| Product | | Amount/kg |
|---|---|---|
| Extr. Cynarae e fol aquos. spiss. (Content of dry substance 66.9%, corresponding to dry substance) | | 834.0(557.9) |
| Glucose sirup Ph. Eur., dried (Content of dry substance 95%, corresponding to dry substance) | | 124.8(118.6) |
| Silicon dioxide, highly dispersed (Aerosil), Ph. Eur | Batch 1 | 20.9 |
| | Batch 2 | 11.5 |
| Maltodextrin Ph. Eur. (DE 11–16) | | 373.0 |

The artichoke leaves extract is in the form of a liquid extract (specifically, it is in a water solvent). This liquid extract was placed into the fluid feed system of a spray dryer, atomized, and combined with the 20.9 g of colloidal silicon dioxide in the drying chamber of the spray dryer. The resultant agglomerated particles were then mixed with the glucose, maltodextrin, and the remaining 11.5 g of colloidal silicon dioxide in a mixer.

The resulting mixture provided a yield of 1036.5 kg with the following composition:
   51.6% Artichoke Leaves extract (Extr. Cynarae e fol aquos. spiss)
   10.9% Glucose sirup Ph. Eur., dried
   34.5% Maltodextrin Ph. Eur.
   3.0% Silicon dioxide, highly dispersed (Aerosil), Ph. Eur.

EXAMPLE 2

Agglomerated particles of ginseng extract/Prosolv SMCC 90/silicon dioxide were prepared with the following ingredients:

| Product | Amount/kg |
|---|---|
| Extr. Ginseng e rad. spir. spiss. (Content of dry substance 73.0%, corresponding to dry substance:) | 50.0(36.5) |
| Extr. Ginseng e rad. spir. spiss. (Content of dry substance 72.0%, corresponding to dry substance:) | 50.0(36.0) |
| Prosolv SMCC 90 | 25.9 |
| Silicon dioxide, highly dispersed (Aerosil), Ph. Eur. | 5.2 |

The ginseng extract is in the form of a liquid extract (specifically, it is in an Ethanol 60% (V/V) solvent). This liquid extract was placed into the fluid feed system of a spray dryer, atomized, and combined with the Prosolv SMCC 90 and colloidal silicon dioxide in the drying chamber of the spray dryer. In this example, the Prosolv SMCC and colloidal silicon dioxide (both dry) were homogenized (in a mixer), and then fed into the drying chamber along with the recycled fines from the collection system.

The agglomerated particles collected from the collection system provided a yield of 94.4 kg, with the following composition:
70.0% Ginseng extract (Extr. Ginseng e rad. spir. spiss.)
25.0% Prosolv SMCC 90
5.0% Silicon dioxide, highly dispersed

COMPARATIVE EXAMPLE B

A mixture of ginseng extract/maltodextrin was prepared with the following ingredients:

| Product | | Amount/kg |
|---|---|---|
| Radix Ginseng, >=7% Ginsenosides (HPLC), >=50% Ratio of Rg1 to Rb1: | | |
| | batch 1 | 110 |
| | batch 2 | 550 |
| | batch 3 | 867 |
| | batch 4 | 842 |
| | | (=526 kg native extract) |
| Maltodextrin USP | | 18 |
| total amount | | 544 |

The ginseng extract is in the form of a liquid extract (specifically, it is in an Ethanol 70% (V/V) solvent). The liquid extract was mixed with the maltodextrin in a mixture, then dried in a vacuum belt dryer and milled. The resultant product had a yield of 517.5 kg, with the following composition:
96.7% Ginseng extract
3.3% maltodextrin USP

EXAMPLE 3

Agglomerated particles of St. John's Wort extract/Prosolv SMCC 90 were prepared with the following ingredients:

| Product | Amount/kg |
|---|---|
| Extr. Hyperici e herb. spir. spiss. (Content of dry substance 48.7%, corresp. to dry substance) | 216.0(105.2) |
| Prosolv SMCC 90 | 45.1 |

The St. John's Wort extract is in the form of a liquid extract (specifically, it is in an Ethanol 60% (m/m) solvent). This liquid extract was placed into the fluid feed system of a spray dryer, atomized, and combined with the Prosolv SMCC 90 in the drying chamber of the spray dryer. In this example, dry Prosolv SMCC (dry) was fed into the drying chamber along with the recycled fines from the collection system.

The agglomerated particles collected from the collection system provided a yield of 138.8 kg, with the following composition:
70% St. John's Wort extract (Extr. Hyperici e herb. spir. spiss.)
30% Prosolv (SMCC 90)

EXAMPLE 4

Agglomerated particles of St. John's Wort extract/Prosolv SMCC 90 were prepared with the following ingredients:

| Product | | Amount/kg |
|---|---|---|
| Extr. Hyperici e herb. spir. spiss. (Content of dry substance 36.3%, corresponding to dry substance:) | | 305.0(110.7) |
| Prosolv SMCC 90 | batch 1 | 2.9 |
| | batch 2 | 48.5 |

The St. John's Wort extract is in the form of a liquid extract (specifically, it is in an Ethanol 60% (m/m) solvent). This liquid extract was placed into the fluid feed system of a spray dryer, atomized, and combined with the Prosolv SMCC 90 in the drying chamber of the spray dryer. In this example, dry Prosolv SMCC (dry) was fed into the drying chamber along with the recycled fines from the collection system.

The agglomerated particles collected from the collection system provided a yield of 176.6 kg, with the following composition:
68.3% St. John's Wort extract (Extr. Hyperici e herb. spir. spiss.)
31.7% Prosolv SMCC 90

EXAMPLE 5

Agglomerated particles of St. John's Wort extract/Prosolv SMCC 90/silicon dioxide were prepared with the following ingredients:

| Product | Amount/kg |
|---|---|
| Extr. Hyperici e herb. spir. spiss. (Content of dry substance 43.0%, corresponding to dry substance:) | 297.5 (127.9) |
| Prosolv SMCC 90 | 45.5 |
| Silicon dioxide, highly dispersed (Aerosil), Ph. Eur | 9.5 |

The St. John's Wort extract is in the form of a liquid extract (specifically, it is in an Ethanol 60% (m/m) solvent). This liquid extract was placed into the fluid feed system of a spray dryer, atomized, and combined with the Prosolv SMCC 90 and colloidal silicon dioxide in the drying chamber of the spray dryer. In this example, the Prosolv SMCC and colloidal silicon dioxide (both dry) were homogenized (in a mixer), and then fed into the drying chamber along with the recycled fines from the collection system.

The agglomerated particles collected from the collection system provided a yield of 152.8 kg, with the following composition:
69.9% St. John's Wort extract (Extr. Hyperici e herb. spir. spiss.)
24.9% Prosolv (SMCC 90)
5.2% Silicon dioxide, highly dispersed (Aerosil), Ph. Eur.

COMPARATIVE EXAMPLE C

A mixture of St. John's extract/maltodextrin/silicon dioxide was prepared with the following ingredients:

| Product | Amount/kg |
| --- | --- |
| Extr. Hyperici e herb. spir. spiss. (Content of dry substance 40.5%, corresponding to dry substance:) | 5000.0(2025.0) |
| Silicon dioxide, highly dispersed (Aerosil), Ph. Eur. | 104.6 |
| Maltodextrin Ph. Eur. | 100.0 |

The St. John's Wort extract is in the form of a liquid extract (specifically, it is in a Ethanol 60% (m/m) solvent). This liquid extract was placed into the fluid feed system of a spray dryer, atomized, and combined with the colloidal silicon dioxide in the drying chamber of the spray dryer. The resultant agglomerated particles were then mixed with the maltodextrin in a mixer.

The mixture provided a yield of 2109.8 kg, with the following composition:
90.8% St. John's Wort extract (Extr. Hyperici e herb. spir. spiss.)
4.7% Silicon dioxide, highly dispersed, Ph. Eur.
4.5% Maltodextrin Ph. Eur.

COMPARATIVE EXAMPLE D

A mixture of St. John's extract/maltodextrin/silicon dioxide was prepared with the following ingredients:

| Product | | Amount/kg |
| --- | --- | --- |
| Extr. Hyperici e herb. spir. spiss. (Content of dry substance 42.4%, corresponding to dry substance:) | | 402.2(170.5) |
| Extr. Hyperici e herb. spir. spiss. (Content of dry substance 42.6%, corresponding to dry substance) | | 367.6(156.6) |
| Extr. Hyperici e herb. spir. spiss. (Content of dry substance 42.2%, corresponding to dry substance::) | | 540.2(227.9) |
| Extr. Hyperici e herb. spir. spiss. (Content of dry substance 63.2%, corresponding to dry substance::) | | 722.3(456.5) |
| Silicon dioxide, highly dispersed, (Aerosil) Ph. Eur. | Batch 1 | 12.3 |
| | Batch 2 | 8.0 |
| | Batch 3 | 39.6 |
| Maltodextrin Ph. Eur. | Batch 1 | 557.8 |
| | Batch 2 | 3.7 |

The St. John's Wort extract is in the form of a liquid extract (specifically, it is in a Ethanol 60% (m/m) solvent). This liquid extract was placed into the fluid feed system of a spray dryer, atomized, and combined with the colloidal silicon dioxide (Batches 1–3) in the drying chamber of the spray-dryer. The resultant agglomerated particles were then mixed with the maltodextrin (Batches 1–2) in a mixer.

The mixture provided a yield of 1588,2 kg, with the following composition:
62.0% St. John's Wort extract (Extr. Hyperici e herb. spir. spiss.)
34.4% Maltodextrin Ph. Eur.
3.6% Silicon dioxide Ph. Eur.

EXAMPLE 6

In Example 6, the agglomerated particles of Example 3 are mixed in a Patterson-Kelley twin-shell V-blender with MgStearate and Maltodextrin to form a mixture with the following composition:

| Ingredient | amount(g) | percentage |
| --- | --- | --- |
| Example 3 | 278.60 | 69.65% |
| Maltodextrin | 119.40 | 29.85% |
| Mg Stearate | 2.00 | 0.50% |
| Total | 400.00 | 100% |

EXAMPLE 7

In Example 7, the agglomerated particles of Example 3 are mixed in a Patterson-Kelley twin-shell V-blender with MgStearate and Prosolv SMCC 50 to form a mixture with the following composition:

| Ingredient | amount (g) | percentage |
| --- | --- | --- |
| Example 3 | 306.69 | 76.67% |
| PROSOLV SMCC 50 | 91.31 | 22.83% |
| Mg Stearate | 2.00 | 0.50% |
| Total | 400.00 | 100% |

COMPARATIVE EXAMPLE E

In Example E, the mixture Example D is mixed in a Patterson-Kelley twin-shell V-blender with MgStearate and Prosolv SMCC 50 to form a mixture with the following composition:

| Ingredient | amount(g) | percentage |
|---|---|---|
| Example D | 278.60 | 69.65% |
| PROSOLV SMCC 50 | 119.40 | 29.85% |
| Mg Stearate | 2.00 | 0.50% |
| Total | 400.00 | 100% |

EXAMPLE 8

In Example 8, the agglomerated particles of Example 3 are mixed in a Patterson-Kelley twin-shell V-blender with MgStearate to form a mixture with the following composition:

| Ingredient | amount(g) | percentage |
|---|---|---|
| Example 3 | 398.00 | 99.50% |
| Mg Stearate | 2.00 | 0.50% |
| Total | 400.00 | 100% |

COMPARATIVE EXAMPLE F

In Example F, the mixture of Example D is mixed in a Patterson-Kelley twin-shell V-blender with MgStearate to form a mixture with the following composition:

| Ingredient | amount(g) | percentage |
|---|---|---|
| Example D | 398.00 | 99.50% |
| Mg Stearate | 2.00 | 0.50% |
| Total | 400.00 | 100% |

EXAMPLE 9

In Example 9-1, the agglomerated particles of Example 5 are mixed in a Patterson-Kelley twin-shell V-blender with Explotab for ten minutes and then MgStearate is added to the mixture and blended for 5 minutes to form a mixture with the following composition:

| Ingredient | amount | percentage |
|---|---|---|
| Example 5 | 386 | 96.50% |
| Explotab | 12 | 3.00% |
| Mg Stearate | 2 | 0.50% |
| Total | 400 | 100% |

In Example 9-2, the agglomerated particles of Example 5 are mixed in a Patterson-Kelley twin-shell V-blender with Explotab for ten minutes and then MgStearate is added to the mixture and blended for 5 minutes to form a mixture with the following composition:

| Ingredient | amount | percentage |
|---|---|---|
| Example 5 | 723.75 | 96.5% |
| Explotab | 22.50 | 3.0% |
| Mg Stearate | 3.75 | 0.5% |
| Total | 750.00 | 100% |

COMPARATIVE EXAMPLE G

In Example G, the mixture of the of Example A is mixed in a Patterson-Kelley twin-shell V-blender with Prosolv SMCC 50, sodium stearyl fumate and MgStearate to form a mixture with the following composition:

| Ingredient | amount(g) | percentage |
|---|---|---|
| Example A | 384 | 96.00% |
| sodium stearyl fumate | 8 | 2.00% |
| talc | 8 | 2.00% |
| Total | 400 | 100% |

EXAMPLE 10

Example 10 was produced in the same manner as Examples 3 and 4, except that the agglomerated particles collected from the collection system had the following composition:
80.0% St. John's Wort extract (Extr. Hyperici e herb. spir. spiss.)
20.0% Prosolv SMCC 90

EXAMPLE 11

Example 11 was produced in the same manner as Examples 3 and 4, except that the agglomerated particles collected from the collection system had the following composition:
75.0% St. John's Wort extract (Extr. Hyperici e herb. spir. spiss.)
25.0% Prosolv SMCC 90

EXAMPLE 12

In Example 12, the agglomerated particles of Example 4 are mixed in a Patterson-Kelley twin-shell V-blender with Explotab for ten minutes and then MgStearate is added to the mixture and blended for 5 minutes to form a mixture with the following composition:

| Ingredient | amount(g) | percentage |
|---|---|---|
| Example 4 | 723.75 | 96.5% |
| Explotab | 22.50 | 3.0% |
| Mg Stearate | 3.75 | 0.5% |
| Total | 750.00 | 100% |

COMPARATIVE EXAMPLE H

In Example H, the mixture of Comparative Example D is mixed in a Patterson-Kelley twin-shell V-blender with Explotab for ten minutes and then MgStearate is added to the mixture and blended for 5 minutes to form a mixture with the following composition:

| Ingredient | amount(g) | percentage |
|---|---|---|
| Example D | 723.75 | 96.5% |
| Explotab | 22.50 | 3.0% |
| Mg Stearate | 3.75 | 0.5% |
| Total | 750.00 | 100% |

EXAMPLE 13

In Example 13, the agglomerated particles of Example 11 are mixed in a Patterson-Kelley twin-shell V-blender with Explotab for ten minutes and then MgStearate is added to the mixture and blended for 5 minutes to form a mixture with the following composition:

| Ingredient | amount | percentage |
|---|---|---|
| Example 11 | 723.75 | 96.5% |
| Explotab | 22.50 | 3.0% |
| Mg Stearate | 3.75 | 0.5% |
| Total | 750.00 | 100% |

EXAMPLE 14

In Example 14, the agglomerated particles of Example 10 are mixed in a Patterson-Kelley twin-shell V-blender with Explotab for ten minutes and then MgStearate is added to the mixture and blended for 5 minutes to form a mixture with the following composition:

| Ingredient | amount(g) | percentage |
|---|---|---|
| Example 10 | 723.75 | 96.5% |
| Explotab | 22.50 | 3.0% |
| Mg Stearate | 3.75 | 0.5% |
| Total | 750.00 | 100% |

COMPARATIVE EXAMPLE I

In Example I, the mixture of Example B is mixed in a Patterson-Kelley twin-shell V-blender for five minutes with Prosolv SMCC 50, sodium stearyl fumate and MgStearate to form a mixture with the following composition:

| Ingredient | amount(g) | percentage |
|---|---|---|
| Example B | 264 | 66.00% |
| sodium stearyl fumate | 8 | 2.00% |
| talc | 8 | 2.00% |
| Prosolv SMCC 50 | 120 | 30.00% |
| Total | 400 | 100% |

COMPARATIVE EXAMPLE J

In Example J, the mixture of Example B is mixed in a Patterson-Kelley twin-shell V-blender with Prosolv SMCC 50 to form a mixture with the following composition:

| Ingredient | amount(g) | percentage |
|---|---|---|
| Example B | 66.92 | 70.00% |
| Prosolv SMCC 50 | 28.68 | 30.00% |
| Total | 95.6 | 100% |

EXAMPLE 15

In Example 15, the agglomerated particles of Example 2 are mixed in a Patterson-Kelley twin-shell V-blender with sodium stearyl fumate and MgStearate for five minutes to form a mixture with the following composition:

| Ingredient | amount(g) | percentage |
|---|---|---|
| Example 2 | 384 | 96.00% |
| sodium stearyl fumate | 8 | 2.00% |
| talc | 8 | 2.00% |
| Total | 400 | 100% |

EXAMPLE 16

In Example 16, the agglomerated particles of Example 1 are mixed in a Patterson-Kelley twin-shell V-blender with sodium stearyl fumate and MgStearate for five minutes to form a mixture with the following composition:

| Ingredient | amount(g) | percentage |
|---|---|---|
| Example 1 | 384 | 96.00% |
| sodium stearyl fumate | 8 | 2.00% |
| talc | 8 | 2.00% |
| Total | 400 | 100% |

The examples set forth above were subjected to tests to evaluate their flow characteristics, moisture uptake characteristics, and compaction characteristics. The results are described below in connection with FIGS. 2 through 13.

St. John's Wort Extract Formulations

Figure 2:
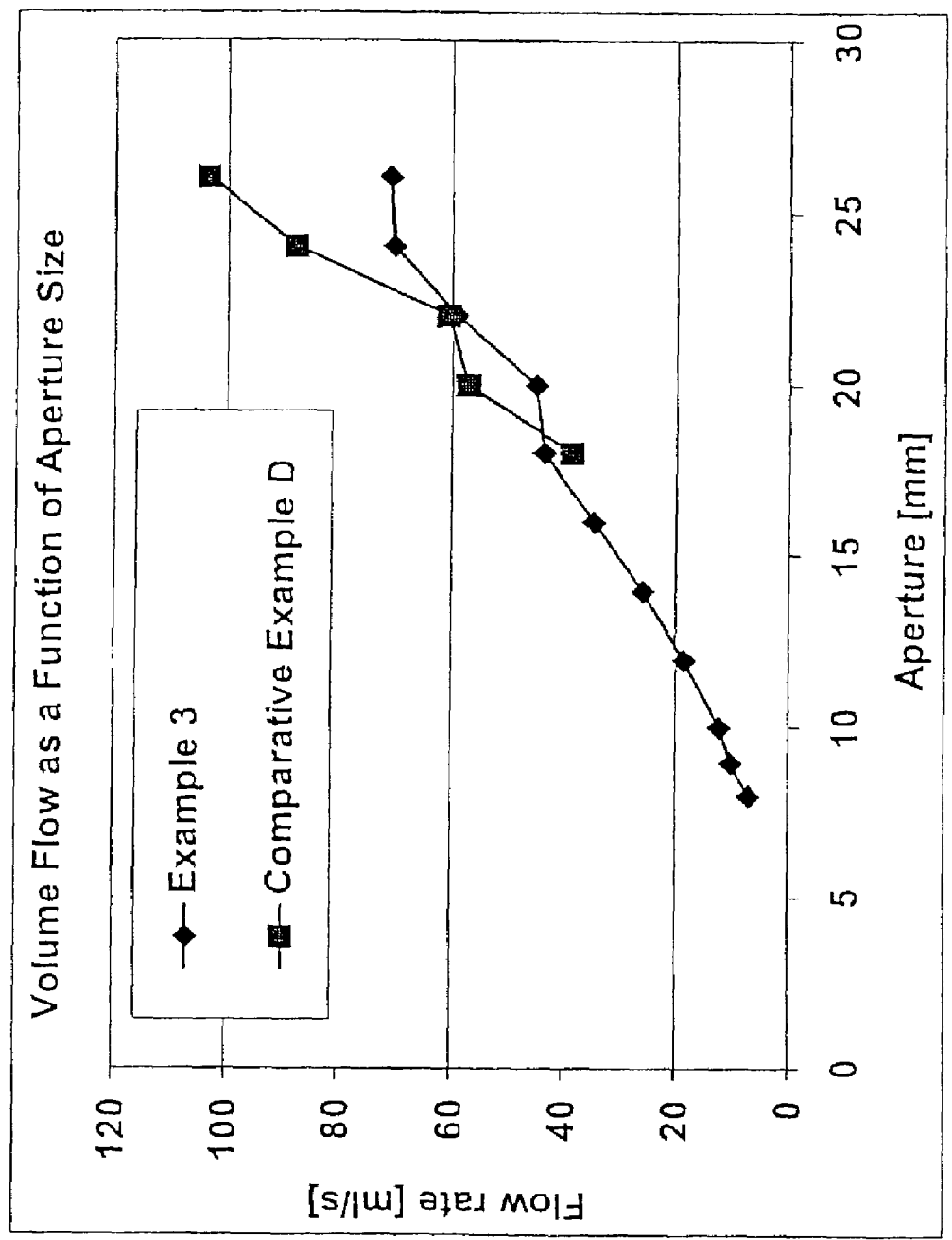
FIG. 2 is a graph of volume flow (ml/s) as a function of aperture size (mm) for the St. John's Wort compositions of Examples 3 and D.

FIG. 2 is a graph of volume flow (ml/s) as a function of aperture size (mm) for the St. John's Wort compositions of Examples 3 and D. The compositions of Example 3 and Example D each had an initial mass of 75.00 g and a bulk density 0.465 g/ml. The flodex cup diameter used for each example was 5.7 cm. The relative humidity during the testing of Example 3 was 65% RH, whereas the relative humidity during the testing of Example D was 45% RH.

Wort extract of Example 3 did not bridge until 7 mm, despite the fact that the testing of Example 3 were conducted at a higher relative humidity.

Figure 3:
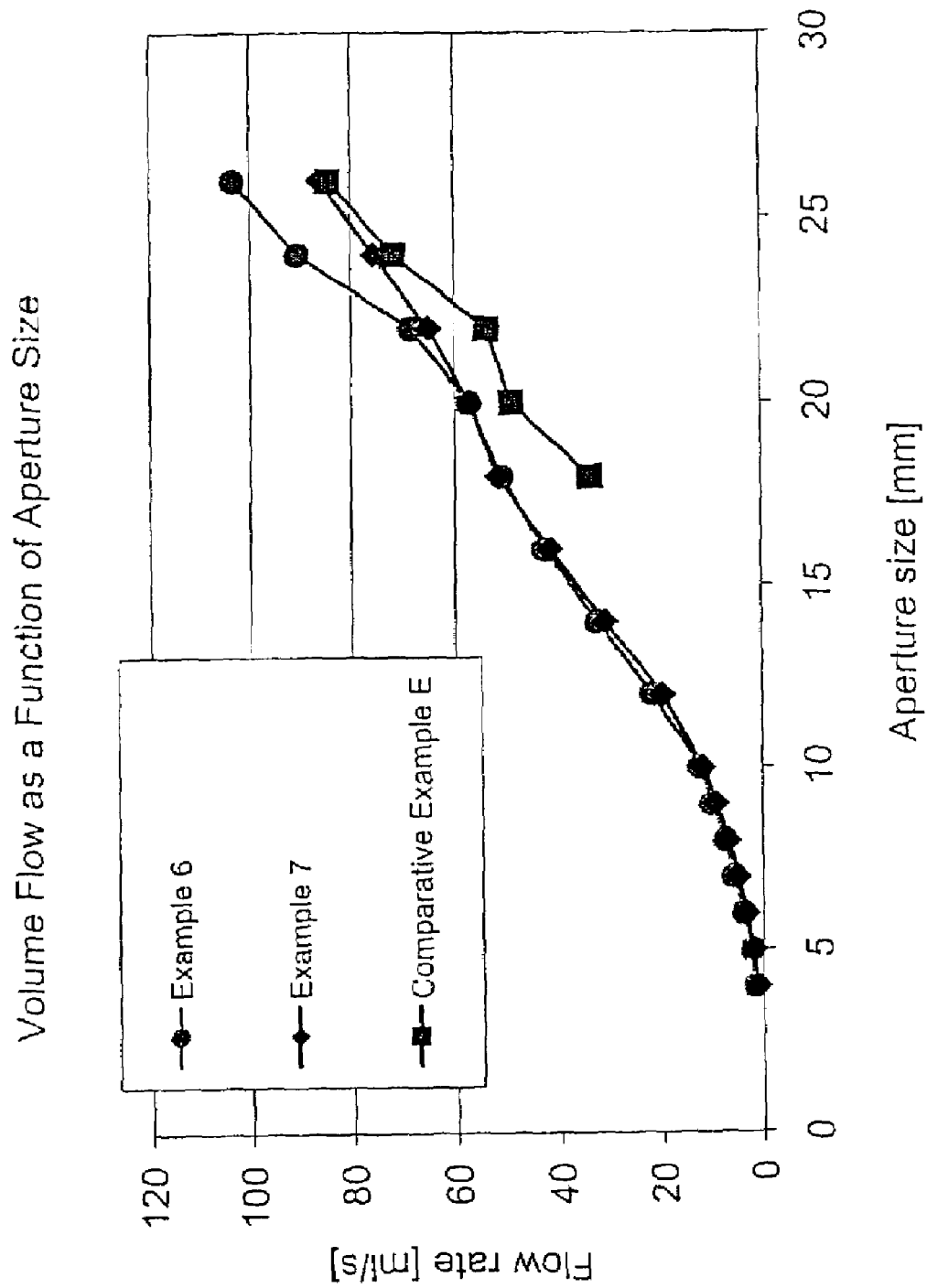
FIG. 3 is a graph of volume flow (ml/s) as a function of aperture size (mm) for the St. John's Wort compositions of Examples 6, 7, and E.

FIG. 3 is a graph of volume flow (ml/s) as a function of aperture size (mm) for the St. John's Wort compositions of Flow Data for Example 3

| Apert. (mm) | Trial 1 time (s) | Trial 1 mass (g) | Trial 2 time (s) | Trial 2 mass (g) | Trial 3 time (s) | Trial 3 mass (g) | Mass flow rate (g · s − 1) | Volume flow rate (ml · s − 1) | Avg. retained mass (g) | Drained angle of repose |
|---|---|---|---|---|---|---|---|---|---|---|
| 26 | 2.00 | 66.50 | 1.87 | 65.90 | 2.19 | 66.50 | 32.95 | 70.89 | 8.70 | 33* |
| 24 | 1.75 | 64.80 | 2.00 | 64.90 | 2.41 | 67.60 | 32.51 | 69.94 | 9.23 | 34* |
| 22 | 2.59 | 65.20 | 2.09 | 66.00 | 2.55 | 66.00 | 27.55 | 59.26 | 9.27 | 33* |
| 20 | 3.03 | 62.20 | 3.05 | 64.80 | 2.88 | 60.90 | 20.97 | 45.12 | 12.37 | 39* |
| 18 | 3.08 | 62.40 | 3.15 | 63.40 | 3.09 | 63.20 | 20.28 | 43.63 | 12.00 | 37* |
| 16 | 3.66 | 61.00 | 3.97 | 62.00 | 3.75 | 62.00 | 16.27 | 35.01 | 13.33 | 39* |
| 14 | 5.53 | 60.70 | 4.69 | 60.60 | 4.69 | 58.60 | 12.13 | 26.10 | 15.03 | 41* |
| 12 | 6.85 | 59.20 | 6.44 | 58.00 | 6.88 | 57.90 | 8.69 | 18.69 | 16.63 | 43* |
| 10 | 9.65 | 54.60 | 9.75 | 53.30 | 9.62 | 57.60 | 5.70 | 12.27 | 19.83 | 47* |
| 9 | 11.63 | 54.50 | 11.69 | 54.90 | 11.94 | 55.90 | 4.69 | 10.09 | 19.90 | 46* |
| 8 | 16.18 | 55.50 | 16.44 | 56.10 | 15.94 | 48.80 | 3.30 | 7.10 | 21.53 | 48* |

Flow Data for Example D

| Apert. (mm) | Trial 1 time (s) | Trial 1 mass (g) | Trial 2 time (s) | Trial 2 mass (g) | Trial 3 time (s) | Trial 3 mass (g) | Mass flow rate (g · s − 1) | Volume flow rate (ml · s − 1) | Avg. retained mass (g) | Drained angle of repose |
|---|---|---|---|---|---|---|---|---|---|---|
| 26 | 1.53 | 70.17 | 1.38 | 67.30 | 1.47 | 73.20 | 48.14 | 103.58 | 4.78 | 20* |
| 24 | 1.69 | 70.30 | 1.68 | 66.30 | 1.60 | 66.00 | 40.77 | 87.72 | 7.47 | 28* |
| 22 | 2.12 | 62.30 | 2.63 | 64.90 | 2.1 | 63.60 | 28.12 | 60.49 | 11.40 | 38* |
| 20 | 2.1 | 59.70 | 2.47 | 62.40 | 2.44 | 62.40 | 26.42 | 56.85 | 13.50 | 42* |
| 18 | 3.41 | 61.70 | 3.28 | 56.90 | 3.15 | 58.40 | 17.99 | 38.71 | 16.00 | 45* |
| 16 | Bridged | | | | | | | | | |

As shown in FIG. 2, the St. John's Wort extract coprocessed with silicified MCC in accordance with the present invention (Example 3) exhibits superior flow characteristics to the St. John's Wort which is not coprocessed with silicified MCC (Comparative Example D). In particular, the St. John's Wort of Example D that was co-sprayed dried with silicon dioxide, and thereafter mixed with maltodextrin was unable to flow though a 16 mm aperture (in other words, Example D bridged at 16 mm). In contrast, the St. John's Wort of Example 3 did not bridge until 7 mm, despite the fact that the testing of Example 3 were conducted at a higher relative humidity.

Examples 6, 7, and E. The flow data was collected using a Hanson FlodeX™ (Hanson Research Instruments, Inc.). The flodex cup diameter used for each composition was 5.7 cm, and each composition had an initial mass of 75.00 g. The composition of Example E had a bulk density of 0.476 g/ml, the composition of Example 6 had a bulk density of 0.468 g/ml, and the composition of Example 7 had a bulk density of 0.432 g/ml. All tests were conducted on the same day, with the relative humidity ranging from 45% to 48% RH.

Flow Data for Example 6

| Apert. (mm) | Trial 1 time (s) | Trial 1 mass (g) | Trial 2 time (s) | Trial 2 mass (g) | Trial 3 time (s) | Trial 3 mass (g) | Mass flow rate (g·s−1) | Volume flow rate (ml·s−1) | Avg. retained mass (g) | Drained angle of repose |
|---|---|---|---|---|---|---|---|---|---|---|
| 26 | 1.28 | 63.50 | 1.23 | 63.60 | 1.43 | 63.10 | 48.48 | 103.59 | 11.60 | 41* |
| 24 | 1.56 | 62.40 | 1.51 | 61.60 | 1.34 | 62.50 | 42.48 | 90.77 | 12.83 | 43* |
| 22 | 1.90 | 60.40 | 1.97 | 60.90 | 1.75 | 58.60 | 32.06 | 68.51 | 15.03 | 46* |
| 20 | 2.28 | 60.40 | 2.13 | 58.70 | 2.15 | 57.00 | 26.85 | 57.38 | 16.30 | 47* |
| 18 | 2.44 | 57.20 | 2.19 | 52.90 | 2.25 | 54.20 | 23.90 | 51.06 | 20.23 | 52* |
| 16 | 2.59 | 53.80 | 2.62 | 54.10 | 2.62 | 49.20 | 20.07 | 42.88 | 22.63 | 54* |
| 14 | 3.50 | 53.90 | 3.15 | 48.80 | 3.23 | 48.70 | 15.32 | 32.74 | 24.53 | 55* |
| 12 | 4.38 | 43.00 | 4.54 | 48.70 | 4.34 | 45.20 | 10.32 | 22.05 | 29.37 | 58* |
| 10 | 7.44 | 44.30 | 7.40 | 44.60 | 7.37 | 42.50 | 5.92 | 12.64 | 31.20 | 59* |
| 9 | 10.97 | 49.80 | 8.62 | 41.10 | 8.44 | 43.40 | 4.82 | 10.29 | 30.23 | 58* |
| 8 | 13.50 | 48.70 | 12.59 | 46.30 | 12.35 | 42.90 | 3.59 | 7.66 | 29.03 | 56* |
| 7 | 16.35 | 44.30 | 15.53 | 46.40 | 14.72 | 42.10 | 2.85 | 6.09 | 30.73 | 57* |
| 6 | 22.06 | 42.40 | 21.22 | 40.80 | 21.44 | 41.00 | 1.92 | 4.10 | 33.60 | 59* |
| 5 | 34.18 | 40.60 | 35.13 | 40.90 | 38.18 | 40.00 | 1.13 | 2.42 | 34.50 | 59* |
| 4 | 52.47 | 38.80 | 50.91 | 37.00 | 37.00 | 39.90 | 0.85 | 1.81 | 36.43 | 60* |

Flow Data for Example 7

| Apert. | Trial 1 time | Trial 1 mass | Trial 2 time | Trial 2 mass | Trial 3 time | Trial 3 mass | Mass flow rate | Volume flow rate | Avg. retained mass | Drained angle of repose |
|---|---|---|---|---|---|---|---|---|---|---|
| 26 | 1.63 | 63.20 | 1.91 | 62.70 | 1.56 | 62.80 | 37.29 | 86.31 | 12.10 | 44* |
| 24 | 1.91 | 58.70 | 1.66 | 61.30 | 1.97 | 60.10 | 32.72 | 75.75 | 14.97 | 49* |
| 22 | 2.50 | 61.50 | 1.97 | 58.60 | 2.00 | 60.00 | 28.12 | 65.08 | 14.97 | 48* |
| 20 | 2.59 | 58.20 | 2.15 | 56.80 | 2.25 | 56.90 | 24.73 | 57.24 | 17.70 | 52* |
| 18 | 2.32 | 54.30 | 2.34 | 54.10 | 2.75 | 56.90 | 22.41 | 51.86 | 19.90 | 54* |
| 16 | 3.16 | 54.20 | 2.91 | 51.60 | 2.85 | 54.70 | 18.03 | 41.73 | 21.50 | 55* |
| 14 | 3.65 | 52.20 | 3.81 | 48.70 | 3.85 | 51.10 | 13.45 | 31.14 | 24.33 | 57* |
| 12 | 6.00 | 52.30 | 6.06 | 50.10 | 5.71 | 50.50 | 8.61 | 19.93 | 24.03 | 55* |
| 10 | 9.69 | 51.50 | 9.85 | 52.40 | 9.18 | 44.40 | 5.16 | 11.94 | 25.57 | 56* |
| 9 | 13.22 | 51.30 | 10.72 | 43.10 | 11.56 | 48.80 | 4.04 | 9.35 | 27.27 | 57* |
| 8 | 15.35 | 49.80 | 13.94 | 40.90 | 14.37 | 41.40 | 3.02 | 6.99 | 30.97 | 60* |
| 7 | 22.37 | 49.80 | 18.34 | 39.40 | 19.72 | 42.90 | 2.18 | 5.05 | 30.97 | 59* |
| 6 | 27.28 | 40.20 | 26.57 | 39.80 | 27.15 | 39.00 | 1.47 | 3.40 | 35.33 | 62* |
| 5 | 44.34 | 39.60 | 41.91 | 39.20 | 48.47 | 43.60 | 0.91 | 2.10 | 34.20 | 61* |
| 4 | 68.06 | 37.50 | 66.15 | 36.40 | 72.43 | 39.60 | 0.55 | 1.27 | 37.17 | 62* |

Flow Data for Example E

| Apert. | Trial 1 time | Trial 1 mass | Trial 2 time | Trial 2 mass | Trial 3 time | Trial 3 mass | Mass flow rate | Volume flow rate | Avg. retained mass | Drained angle of repose |
|---|---|---|---|---|---|---|---|---|---|---|
| 26 | 1.32 | 53.60 | 1.28 | 52.20 | 1.38 | 54.30 | 40.25 | 84.55 | 21.63 | 58* |
| 24 | 1.69 | 51.80 | 1.50 | 53.20 | 1.50 | 54.60 | 34.17 | 71.79 | 21.80 | 57* |
| 22 | 2.38 | 52.10 | 1.75 | 49.80 | 1.90 | 50.50 | 25.64 | 53.87 | 24.20 | 58* |
| 20 | 1.94 | 46.00 | 2.06 | 47.90 | 2.04 | 47.20 | 23.37 | 49.09 | 27.97 | 61* |
| 18 | 3.31 | 46.80 | 2.69 | 41.10 | 2.22 | 42.30 | 16.16 | 33.94 | 31.60 | 63* |
| 16 | BRIDGED | | | | | | | | | |

As shown in FIG. 3, when the St. John's Wort composition of Example 3 is further mixed with maltodextrin and MgStearate (Example 6) or with silicified MCC and Mg Stearate (Example 7), the resultant formulation continued to flow even through the minimum aperture of 4 mm. In contrast, mixing the St. John's Wort extract of Example D with silicified MCC (Example E) had no appreciable effect on flow, as the resultant formulation continued to bridge at 16 mm.

Figure 4:
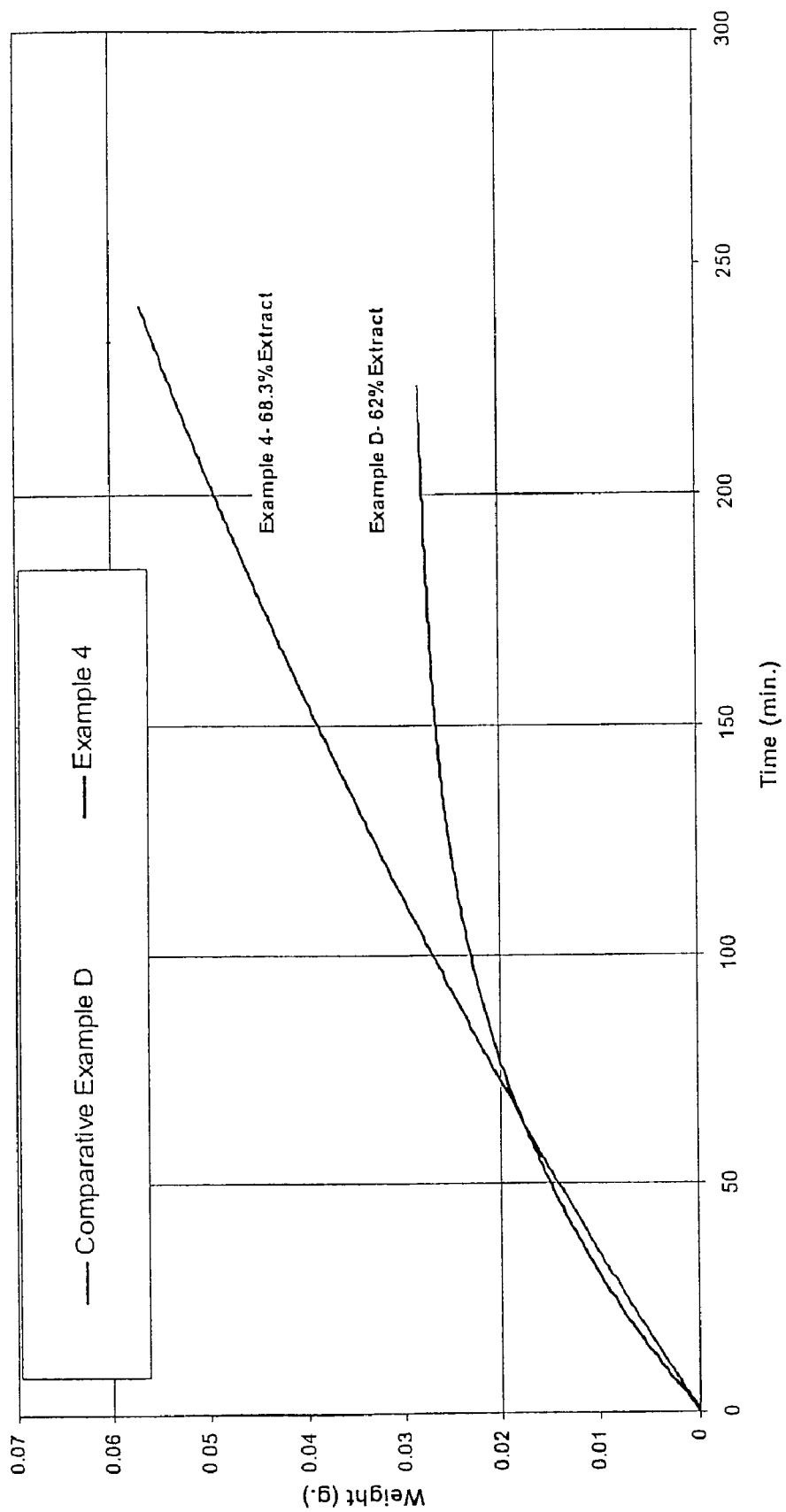
FIG. 4 is a graph of moisture uptake for the St. John's wort compositions of Examples 4 and D.

FIG. 4 is a graph of moisture uptake for the St. John's wort compositions. Twenty-five gram samples of Examples 4 and D were maintained at 25 C. and 40% RH. As shown in FIG. 4, the St. John's Wort extract that was co-sprayed dried with silicified MCC (Example 4) has acceptable moisture uptake when compared the St. John's Wort extract which was not co-spray dried with silicified MCC (Example D). In general, it is considered desirable to have acceptable moisture uptake because unacceptably high levels of moisture absorption may lead to stability problems with the final dosage form, and can cause adverse affects during tableting such as caking.

Figure 5:
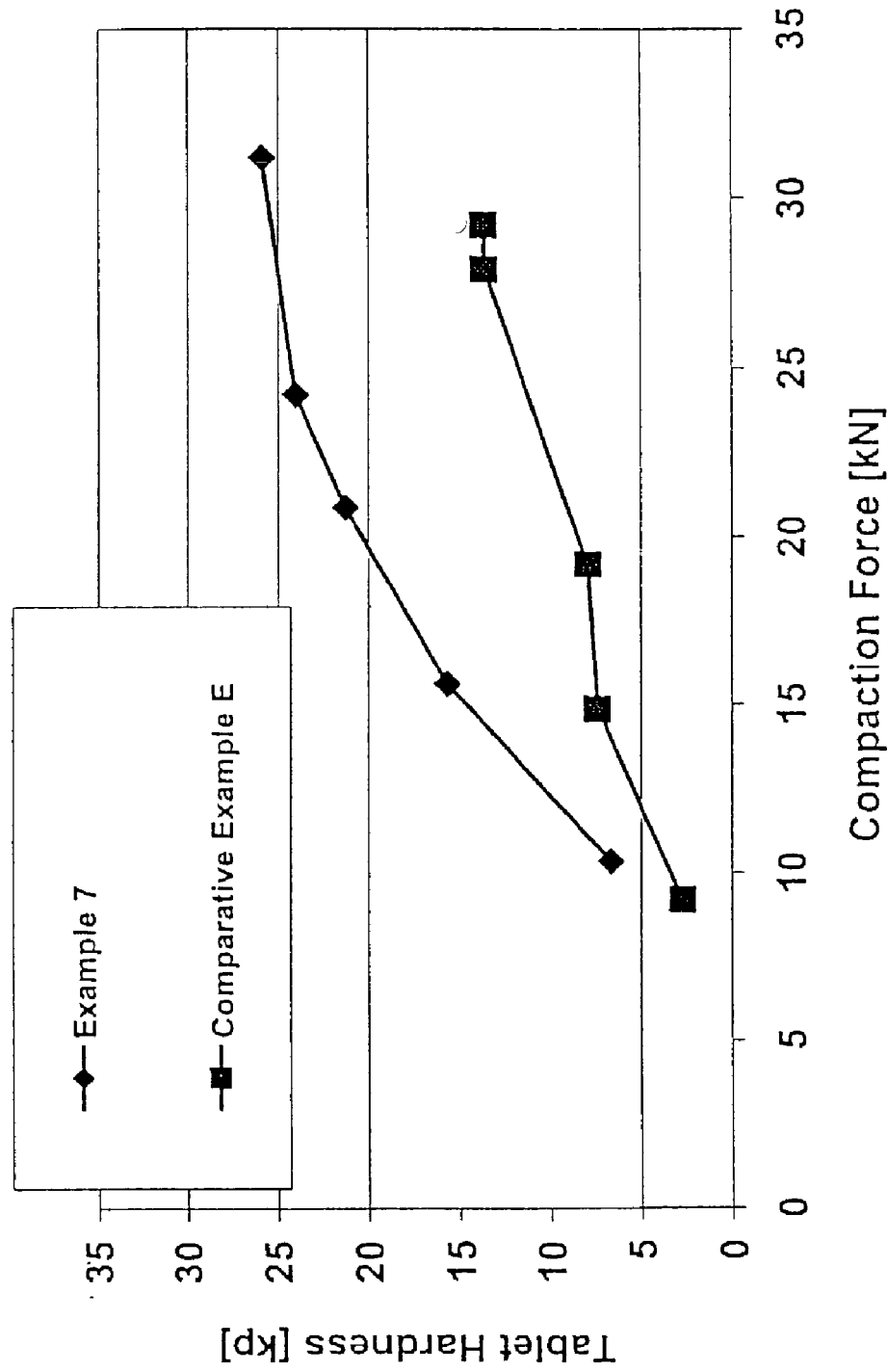
FIG. 5 is a graph of tablet hardness as a function of compaction force for the compositions of Examples 7 and E.
Figure 6:
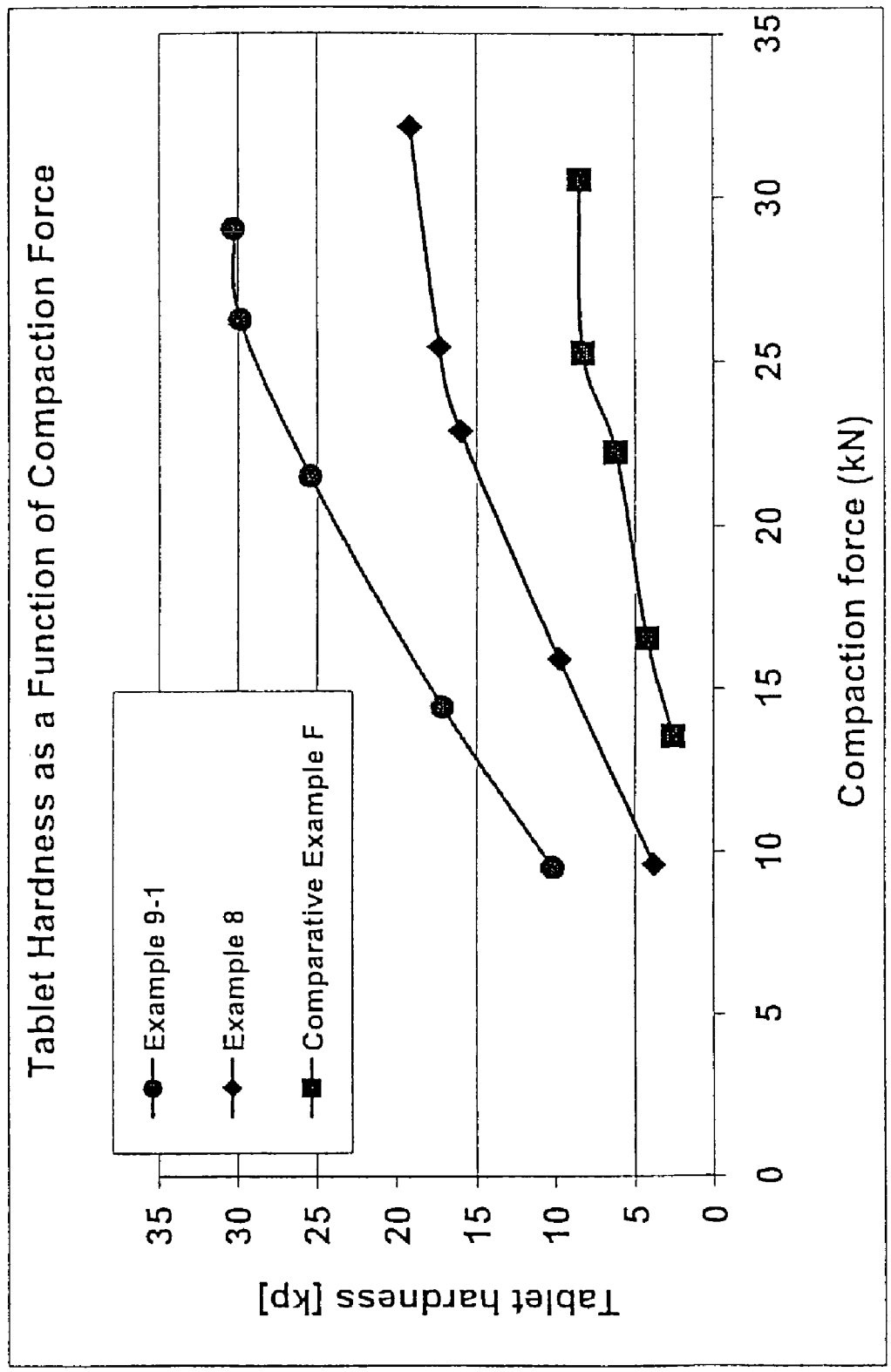
FIG. 6 is a graph of tablet hardness as a function of compaction force for the compositions of Examples 8, 9-1, and F.
Figure 7:
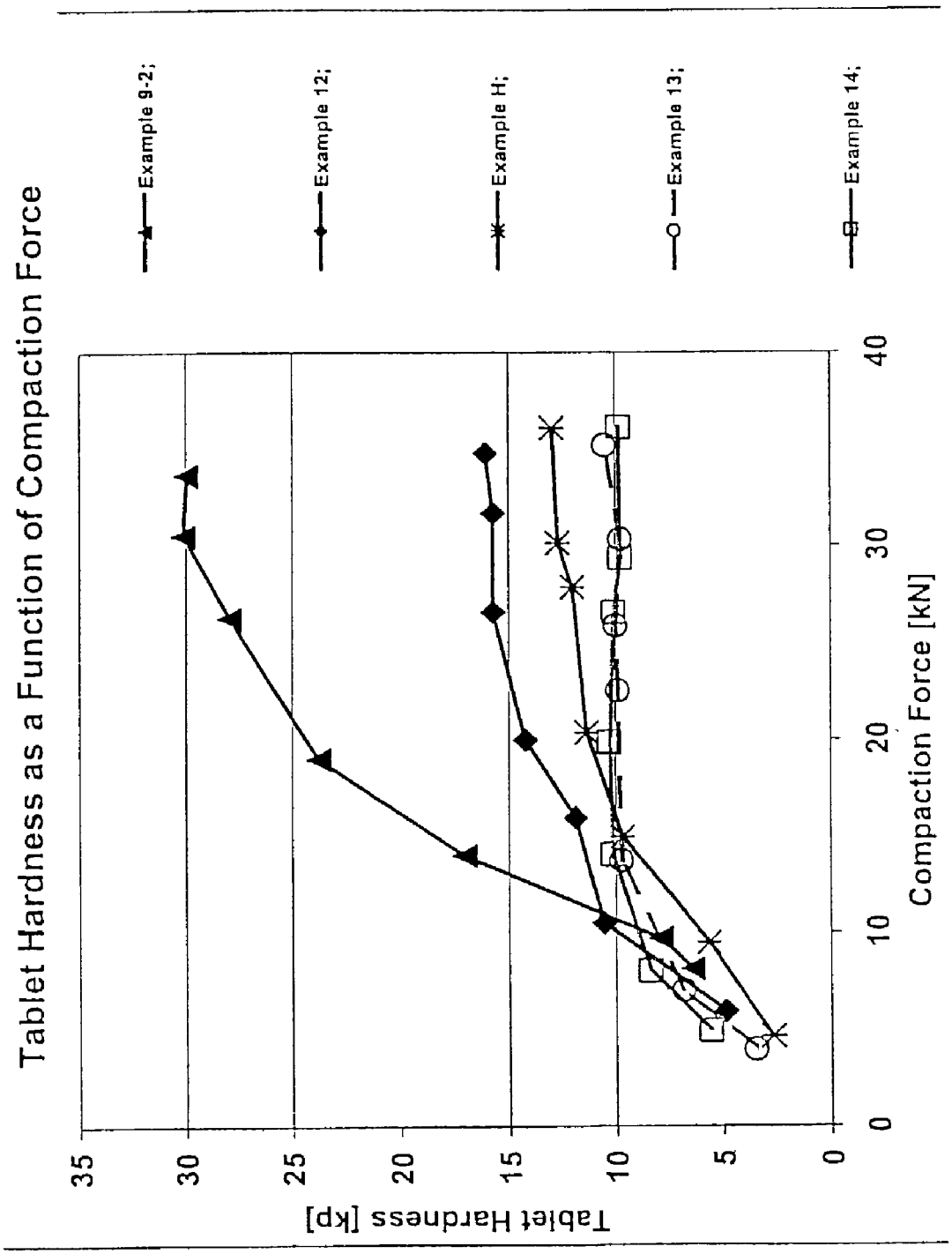
FIG. 7 is a graph of tablet hardness as a function of compaction force for the compositions of Examples 9-2, 12, 13, 14, and H.

FIGS. 5 through 7 are graphs of tablet hardness as a function of compaction force for Examples 7–9, 12–14, and H.

FIG. 5 is a graph of tablet hardness as a function of compaction force for the compositions of Examples 7 and E. Each composition was tableted in a caplet shaped 0.250"× 0.750", and the tablets had a target tablet mass of 550 mg. The compaction data for each formulation is set forth below:

Compaction Data For Example E

| Compaction force (kN) | Std. dev. (kN) | Tablet hardness (kp) | Std. dev. (kp) | Avg. Tablet mass (mg) |
|---|---|---|---|---|
| 9.21 | 0.24 | 2.75 | 0.00 | 553.14 |
| 14.88 | 0.63 | 7.47 | 0.01 | 555.32 |
| 19.19 | 0.52 | 7.99 | 0.01 | 545.62 |
| 27.92 | 0.63 | 13.70 | 0.01 | 554.62 |
| 29.21 | 0.54 | 13.74 | 0.01 | 547.48 |

Compaction Data For Example 7

| Compaction force (kN) | Std. dev. (kN) | Tablet hardness (kp) | Std. dev. (kp) | Avg. Tablet mass (mg) |
|---|---|---|---|---|
| 10.35 | 0.19 | 6.75 | 0.01 | 550.22 |
| 15.62 | 0.20 | 15.75 | 0.00 | 551.01 |
| 20.88 | 0.38 | 21.30 | 0.01 | 548.03 |
| 24.22 | 0.34 | 24.08 | 0.01 | 555.37 |
| 31.18 | 0.26 | 25.91 | 0.00 | 549.99 |

As shown in FIG. 5 and the above data, the St. John's Wort co-spray dried with 30% silicified MCC exhibits superior compaction and hardness characteristics, when tableted with MgStearate and silicified MCC (Example 7), than a St. John's Wort extract that is tableted in the same manner, but is not co-spray dried with silicified MCC (Example E).

FIG. 6 is a graph of tablet hardness as a function of compaction force for the compositions of Examples 8, 9-1, and F. Each composition was tableted in a caplet shaped 0.250"×0.750", and the tablets had a target tablet mass of 550 mg. The compaction data for each formulation is set forth below:

Compaction Data For Example 8

| Compaction force (kN) | Std. dev. (kN) | Tablet hardness (kp) | Std. dev. (kp) | Avg. Tablet mass (mg) |
|---|---|---|---|---|
| 9.61 | 0.04 | 3.83 | 0.00 | 545.81 |
| 15.90 | 0.19 | 9.80 | 0.01 | 545.96 |
| 22.89 | 0.12 | 16.07 | 0.01 | 549.83 |
| 25.45 | 0.10 | 17.39 | 0.00 | 545.44 |
| 32.15 | 0.24 | 19.19 | 0.00 | 545.34 |

Compaction Data For Example 9-1

| Compaction force (kN) | Std. dev. (kN) | Tablet hardness (kp) | Std. dev. (kp) | Avg. Tablet mass (mg) |
|---|---|---|---|---|
| 9.52 | 0.20 | 10.23 | 1.66 | 551.24 |
| 14.43 | 0.62 | 17.18 | 1.66 | 549.67 |
| 21.52 | 1.90 | 25.48 | 2.38 | 547.77 |
| 26.29 | 1.76 | 29.91 | 2.22 | 553.42 |
| 29.06 | 1.64 | 30.35 | 0.96 | 548.12 |

Compaction Data For Example F

| Compaction force (kN) | Std. dev. (kN) | Tablet hardness (kp) | Std. dev. (kp) | Ave. Tablet mass (mg) |
|---|---|---|---|---|
| 13.55 | 2.15 | 2.59 | 0.01 | 554.97 |
| 16.54 | 1.34 | 4.26 | 0.01 | 545.79 |
| 22.25 | 1.04 | 6.26 | 0.01 | 545.78 |
| 25.27 | 0.70 | 8.30 | 0.01 | 552.25 |
| 30.55 | 0.73 | 8.52 | 0.01 | 546.23 |

As shown in FIG. 6 and the above data, the St. John's Wort co-spray dried with 30% silicified MCC exhibits superior compaction and hardness characteristics, when tableted with MgStearate (Example 8), than a St. John's Wort extract that is tableted in the same manner, but is not co-spray dried with silicified MCC (Example F). In addition, when the St. John's Wort that was co-spray dried with silicified MCC and colloidal silicon dioxide (Example 9-1) was tableted with MgStearate and Explotab, it exhibited superior compaction and hardness characteristics to both Example 8 and Example F.

FIG. 7 is a graph of tablet hardness as a function of compaction force for the compositions of Examples 9-2, 12, 13, 14, and H. Each composition was tableted in a caplet shaped 0.2230"×0.5670" and the tablets had a target tablet mass of 441 mg. The compaction data for each formulation is set forth below:

Compaction Data For Example 9-2

| Compaction force (kN) | Std. dev. (kN) | Tablet hardness (kp) | Std. dev. (kp) | Avg. Tablet mass (mg) |
|---|---|---|---|---|
| 8.13 | 1.63 | 6.44 | 0.50 | 443.17 |
| 9.71 | 0.33 | 7.93 | 0.74 | 441.75 |
| 14.03 | 0.32 | 17.06 | 1.46 | 436.69 |
| 18.99 | 0.30 | 23.80 | 8.55 | 434.97 |

-continued

Compaction Data For Example 9-2

| Compaction force (kN) | Std. dev. (kN) | Tablet hardness (kp) | Std. dev. (kp) | Avg. Tablet mass (mg) |
|---|---|---|---|---|
| 26.27 | 0.29 | 27.98 | 2.46 | 435.47 |
| 30.52 | 0.57 | 30.13 | 1.85 | 440.33 |
| 33.71 | 0.38 | 30.00 | 1.99 | 444.91 |

Compaction Data For Example 12

| Compaction force (kN) | Std. dev. (kN) | Tablet hardness (kp) | Std. dev. (kp) | Avg. Tablet mass (mg) |
|---|---|---|---|---|
| 5.95 | 0.12 | 4.90 | 0.91 | 436.09 |
| 10.53 | 0.22 | 10.58 | 0.27 | 446.32 |
| 15.99 | 0.38 | 11.91 | 0.24 | 436.98 |
| 20.00 | 0.49 | 14.25 | 1.15 | 433.90 |
| 26.60 | 0.61 | 15.75 | 0.47 | 441.28 |
| 31.76 | 0.49 | 15.76 | 0.66 | 435.52 |
| 34.84 | 0.69 | 16.09 | 0.53 | 434.59 |

Compaction Data For Example 13

| Compaction force (kN) | Std. dev. (kN) | Tablet hardness (kp) | Std. dev. (kp) | Avg. Tablet mass (mg) |
|---|---|---|---|---|
| 3.97 | 0.43 | 3.50 | 0.78 | 435.09 |
| 7.05 | 0.83 | 6.86 | 0.76 | 442.75 |
| 13.80 | 1.24 | 9.76 | 0.25 | 438.2 |
| 22.56 | 1.42 | 9.92 | 0.45 | 442.01 |
| 25.92 | 1.29 | 10.02 | 0.42 | 443.17 |
| 30.39 | 0.73 | 9.79 | 0.33 | 436.73 |
| 35.28 | 2.64 | 10.53 | 0.26 | 442.37 |

Compaction Data For Example 14

| Compaction force (kN) | Std. dev. (kN) | Tablet hardness (kp) | Std. dev. (kp) | Avg. Tablet mass (mg) |
|---|---|---|---|---|
| 4.98 | 0.22 | 5.59 | 0.79 | 436.18 |
| 8.06 | 0.82 | 8.40 | 0.44 | 436.08 |
| 14.11 | 0.79 | 10.15 | 0.35 | 437.70 |
| 19.92 | 2.05 | 10.28 | 0.42 | 438.96 |
| 26.61 | 3.22 | 10.08 | 0.79 | 440.82 |
| 29.40 | 0.96 | 9.77 | 0.86 | 436.35 |
| 36.21 | 1.76 | 9.86 | 1.04 | 437.68 |

Compaction Data For Example H

| Compaction force (kN) | Std. dev. (kN) | Tablet hardness (kp) | Std. dev. (kp) | Avg. Tablet mass (mg) |
|---|---|---|---|---|
| 4.63 | 0.24 | 2.70 | 0.20 | 439.39 |
| 9.51 | 0.39 | 5.67 | 0.40 | 437.44 |
| 15.02 | 0.94 | 9.68 | 0.50 | 436.26 |
| 20.38 | 0.47 | 11.38 | 0.36 | 435.15 |
| 27.88 | 0.82 | 12.05 | 0.52 | 435.01 |
| 30.17 | 0.99 | 12.74 | 0.31 | 445.15 |
| 36.15 | 0.59 | 13.00 | 0.61 | 442.29 |

FIG. 7 shows a comparison of the compaction characteristics of i) St. John's Wort extract co-spray dried with 24.9% silicified MCC and 5.2% silicon dioxide (Example 5), ii) St. John's Wort extract co-spray dried with 31.7% silicified MCC (Example 4); iii) St. John's Wort extract which is not co-spray dried with silicified MCC (Example C); iv) St. John's Wort extract co-spray dried with 25% silicified MCC and no silicon dioxide (Example 11); and v) St. John's Wort extract co-spray dried with 20% silicified MCC (Example 10); wherein each formulation was blended with 3% Explotab and 0.5% MgStearate to obtain the mixture of Examples 9-2, 12, H, 13, and 14 respectively, and then tableted.

As shown in FIG. 7, the formulation of Example 9-2 (co-spray dried with silicified MCC and silicon dioxide) provided the best compaction characteristics. The compaction characteristics of the formulation of Example 12 (co-spray dried with 31% silicified MCC) were far worse than the formulation of Example 9-2, but still significantly better than Comparative Example H (not co-spray dried with silicified MCC). Interestingly, however, the compaction characteristics of the formulations of Example 13 (co-spray dried with 25% silicified MCC) and Example 14 (co-spray dried with 20% silicified MCC) were worse than Examples 9-2 and 12, and were, in fact, comparable to the formulation of Comparative Example H.

Ginseng Extract Formulations

FIG. 8 is a graph of moisture uptake for the Ginseng extract compositions of Examples 2 and B. Twenty-five gram samples of Examples B and 2 were maintained at 25 C. and 40% RH. As shown in FIG. 8, the ginseng extract that was co-sprayed dried with silicified MCC (Example 2) absorbed about 40% less moisture over 240 minutes as the ginseng extract which was not co-spray dried with silicified MCC. However, in view of the fact that the composition of Example 2 includes 17.5 grams of Ginseng extract (0.70*25), whereas the composition of Example B includes 24.175 g of Ginseng extract (0.967*25), a "weight corrected" plot for Example 2 is also included in FIG. 8. The data for "Example 2 with Weight Correction" in FIG. 8 was obtained by multiplying each data point of Example 2 by 24.175/17.5. Based upon the above, the Ginseng extract that was co-sprayed dried with silicified MCC (Example 2) has acceptable moisture uptake when compared the St. John's Wort extract which was not co-spray dried with silicified MCC (Example B)

FIG. 9 is a graph of mass flow (g/s) as a function of aperture size (mm) for the Ginseng composition of Example 2. Flow data was collected using a Hanson Flodex™ (Hanson Research Instruments, Inc.). Flow data was collected for the composition of Example 2 and the composition of Example B blended with 30% Prosolv SMCC 50 (Example J). It should be appreciated that in view of the fact that the composition of Example B is 96.7% ginseng extract, it was blended with 30% Prosolv SMCC 50 for purposes of comparison with Example 2, which contains 70% ginseng extract. The flodex cup diameter used for each composition was 5.7 cm, each composition had an initial mass of 95.6 g, and the experiment was conducted at 62% RH. The flow data for Example 2 is as follows:

Flow Data for Example 2

| Aperture (mm) | Trial 1 time (s) | Trial 1 mass (g) | Trial 2 time (s) | Trial 2 mass (g) | Trial 3 time (s) | Trial 3 mass (g) | Mass flow rate (g·s−1) |
|---|---|---|---|---|---|---|---|
| 26 | 2.10 | 66.50 | 2.00 | 61.80 | 2.20 | 63.00 | 30.37 |
| 22 | 2.30 | 59.90 | 2.00 | 55.90 | 1.90 | 58.80 | 28.16 |
| 18 | 3.20 | 45.30 | 2.80 | 48.20 | 3.30 | 50.50 | 15.48 |
| 14 | 6.6 | 47.6 | 5.8 | 47.8 | 5.3 | 46.8 | 8.03 |
| 12 | 8.5 | 46.9 | 8.9 | 41.5 | 6.5 | 40.9 | 5.41 |
| 10 | 14.8 | 46.1 | 11.7 | 41.5 | 12.7 | 43.9 | 3.35 |
| 9 | 12 | 34.6 | 15.5 | 36.9 | 14.2 | 40.9 | 2.70 |
| 8 | Bridged | | | | | | |

The composition of Example J bridged at 30 mm, and, therefore, is not shown in FIG. 9. In contrast, the Ginseng composition of Example 2 bridged at 8 mm. As such, the composition of Example 2 provides superior flow characteristics as compared with the composition of Example B even when Example B is blended with 30% Prosolv SMCC 50 in an attempt to improve its flow characteristics.

FIG. 10 is a graph of tablet hardness as a function of compaction force for the compositions of Examples I and 15. Each composition was tableted in a caplet shaped 0.750"×0.3125", and the tablets had a target tablet mass of 800 mg. The compaction data for each formulation is set forth below:

Compaction Data for Example 15

| Compaction force (kN) | Tablet hardness (kp) |
|---|---|
| 10.4 | 6.8 |
| 15 | 12.7 |
| 20.2 | 19.8 |
| 25.8 | 26.5 |

Compaction Data for Example I

| Compaction force (kN) | Tablet hardness (kp) |
|---|---|
| 9.8 | 14.5 |
| 14 | 23.9 |
| 20.9 | 37.1 |
| 23.7 | 40.2 |

As shown in FIG. 10 and the above data, the Ginseng extract co-spray dried with 25% silicified MCC and 5% colloidal silicon dioxide (Example 15) exhibits acceptable compaction and hardness characteristics.

Atrichoke Leave Extract Formulations

FIG. 11 is a graph of mass flow (g/s) as a function of aperture size (mm) for the Artichoke compositions of Examples 1 and A. Flow data was collected using a Hanson Flodex™ (Hanson Research Instruments, Inc.). The compositions of Example 1 and Example A each had an initial mass of 95.6 g. The flodex cup diameter used for each example was 5.7 cm, and the test was conducted at 24% RH.

Flow Data for Example 1

| Aperture (mm) | Trial 1 time (s) | Trial 1 mass (g) | Trial 2 time (s) | Trial 2 mass (g) | Trial 3 time (s) | Trial 3 mass (g) | Mass flow rate (g·s−1) |
|---|---|---|---|---|---|---|---|
| 20 | 2.80 | 73.91 | 2.80 | 75.67 | 3.10 | 78.64 | 26.23 |
| 16 | 5.80 | 76.59 | 4.50 | 72.49 | 6.40 | 74.38 | 13.38 |
| 12 | 8.60 | 72.21 | 9.30 | 71.58 | 11.40 | 75.53 | 7.49 |
| 10 | 16.40 | 73.15 | 15.00 | 70.72 | 14.30 | 70.96 | 4.70 |
| 8 | 22.60 | 69.73 | 21.20 | 68.40 | 24.70 | 74.22 | 3.10 |
| 6 | 44.20 | 66.75 | 44.60 | 68.45 | 44.80 | 66.45 | 1.51 |
| 4 | 157.00 | 66.45 | 111.10 | 64.40 | 114.20 | 65.60 | 0.51 |

Flow Data for Example A

| Aperture (mm) | Trial 1 time (s) | Trial 1 mass (g) | Trial 2 time (s) | Trial 2 mass (g) | Trial 3 time (s) | Trial 3 mass (g) | Mass flow rate (g·s−1) |
|---|---|---|---|---|---|---|---|
| 20 | 2.10 | 65.88 | 3.60 | 72.54 | 2.50 | 68.35 | 25.22 |
| 16 | 3.20 | 63.10 | 3.90 | 72.14 | 4.70 | 68.42 | 17.26 |
| 12 | 10.30 | 70.17 | 8.60 | 68.23 | 7.60 | 64.82 | 7.67 |
| 10 | 12.70 | 68.24 | 13.60 | 63.55 | 12.60 | 64.57 | 5.05 |
| 8 | 21.20 | 67.43 | 21.50 | 61.73 | 20.90 | 63.93 | 3.04 |
| 5 | 68.00 | 63.79 | 71.10 | 66.95 | 69.40 | 64.75 | 0.94 |
| 4 | 127.00 | 54.90 | 114.30 | 56.83 | 112.00 | 56.99 | 0.48 |

As shown in FIG. 11, the Artichoke extract coprocessed with silicified MCC in accordance with the present invention (Example 1) exhibits equivalent flow characteristics to the artichoke extract which is not coprocessed with silicified MCC (Comparative Example A). It should be noted that equivalent flow characteristics were obtain despite the fact that the formulation of Example 1 had 70% artichoke leaves extract as compared to 51.6% artichoke leaves extract in Example A.

FIG. 12 is a graph of moisture uptake for artichoke extract. Twenty-five gram samples of Examples 1 and A were maintained at 25° C. and 40% RH. As shown in FIG. 12, the artichoke extract that was co-sprayed dried with silicified MCC (Example 1) absorbed over twice as much moisture over 800 minutes than the artichoke extract which was not co-spray dried with silicified MCC. However, despite the fact that the extract of Example 1 absorbed more moisture than the extract of Example A, both extracts were able to flow at aperture sizes as small as 4 mm as demonstrated in FIG. 11.

FIG. 13 is a graph of tablet hardness as a function of compaction force for the compositions of Examples 16 and G. Each composition was tableted in a caplet shaped 0.750"×0.3125", and the tablets had a target tablet mass of 800 mg. The compaction data for each formulation is set forth below:

Compaction Data For Example 16

| Compaction force (kN) | Tablet hardness (kp) |
|---|---|
| 10.3 | 5.4 |
| 15.1 | 10.8 |

-continued

Compaction Data For Example 16

| Compaction force (kN) | Tablet hardness (kp) |
|---|---|
| 19.8 | 15.8 |
| 24.8 | 21.7 |

Compaction Data For Example G

| Compaction force (kN) | Tablet hardness (kp) |
|---|---|
| 10.3 | 2.2 |
| 15.6 | 5.01 |
| 19.6 | 8.1 |
| 25.1 | 12.8 |

As shown in FIG. 13 and the above data, the artichoke extract co-spray dried with 25% silicified MCC and 5% colloidal silicon dioxide exhibits superior compaction and hardness characteristics, when tableted with talc and sodium stearyl fumarate (Example 16), than an Artichoke extract that is tableted in the same manner, but is not co-spray dried with silicified MCC (Example G).

As one of ordinary skill in the art will appreciate, the compaction data set forth above indicates that since the formulations of Examples 7–9, 12, 15 and 16 exhibit superior compaction characteristics to comparative examples E, F, H, I, and K, the formulations in accordance with these examples can be compressed into smaller tablets than their corresponding comparative examples. For example, St. John's Wort is currently marketed in 600 mg capsules, wherein each capsule includes 150 mg. of St. John's Wort extract. In contrast, as shown in the table below, with the formulations of Examples 8 and 9-2, 300 mg of St. John's Wort extract can be included in a 450 mg. tablet (normalizing the compaction data for these examples to a 450 mg. tablet):

| Composition | Actual Amount Active Agent (mg) | Tablet size | Actual Tablet Wt. (mg) | Normalized Tablet Weight | Normalized Amount Active Agent (mg) | Percent Active Agent |
|---|---|---|---|---|---|---|
| Example 9-2 | 297.46993 | 0.2230" × 0.5670 | 441 mg | 450 | 303.54 | 67.4535 |
| Example 8 | 383.075 | 0.250" × 0.750" | 550 mg | 450 | 313.425 | 69.65 |

Similarly, Ginseng is currently marketed in 450 mg tablets, wherein each tablet includes 100 mg. of Ginseng extract. In contrast, as shown in the table below, with the formulations of Example 16, 500 mg of Ginseng extract can be included in a 752 mg. tablet (normalizing the compaction data for this example to a 752 mg. tablet):

| Composition | Actual Amount Active Agent (mg) | Tablet size | Actual Tablet Wt. (mg) | Normalized Tablet Weight | Normalized Amount Active Agent (mg) | Percent Active Agent |
|---|---|---|---|---|---|---|
| Example 16 | 539.628 | 0.750" × 0.3125" | 800 | 752 | 507.250 | 67.4535 |

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A process of creating agglomerated particles containing an herbal extract comprising combining a wetted herbal extract with dry silicified microcrystalline cellulose in a spray dryer and spray drying to form agglomerated particles.

2. The process of claim 1, wherein the herbal extract is hygroscopic.

3. The process of claim 1, wherein the herbal extract is selected from the group consisting of Alfalfa Leaf, Alfalfa Juice, Aloec-emodin, Andrographolide, Angelica Root, Astragalus Root, Bilberry, Black Cohosh Root, Black Walnut Leaf, Blue Cohosh Root, Burdock Root, Cascara Bark, Cats Claw Bark, Catnip Leaf, Cayenne, Chamomile Flowers, Chaste Tree Berries, Chickweed, Chinese Red Sage Root, Cranberry, Chrysophanol, Comfrey Leaf, Cramp Bark, Damiana Leaf, Dandelion Root CO, Devil's Claw Root, Diosgenin, Dong Quai Root, Dong Quai, Echinacea, Echinacea Angustifolia Root, Echinacea Purpurea Herb Root and Echinacca Angust./Purpurea Blend CO, Echinacea Angust./Goldenseal Blend, Eleuthero (Siberian) Ginseng Root, Emodin, Eyebright Herb, Fenugreek, Feverfew Herb CO, Fo- Ti Root, Fo- Ti, Garcinia Cambogia, Gentian Root, Ginger, Ginko Biloba Ginger Root, Ginseng, Ginko Leaf, Ginseng Root, Goldenseal Root, Gotu Kola Herb, Grape Seed, Grape Skin, Green Tea, Green Tea, Decaf, Guarana Seeds, Gynostemma Pentaphyllum, Hawthorn Berries, Hawthorn Leaf, Hesperdin, Hops Flowers, Horehound Herb, Horse Chestnut, Horsetail, Hyssop Leaf, Huperzine A, Juniper Berries, Kava Kava Root, Kola Nut, Lavender Flowers, Lemon Balm, Licorice Root, Lobelia Herb, Lomatium, Marshmallow Root, Milk Thistle Seed, Milk Thistle, Mullein Leaf, Myrrh, Naringin, Neohesperidin, Nettle Leaf, Olive Leaf, Oregon Grape Root, Papain, Parsley Leaf & Root, Passion Flower, Pau D' Arco Bark, Pennyroyal, Peppermint Leaf, Physcion, Polystictus Versicolor Mushroom, Quercetin, Red Clover Blossoms, Red Clover, Red Raspberry Leaf, Red Yeast Rice, Reishi Mushrooms, Rhein, Rhubarb Root, Rosemary Leaf, Rutin, Sarsaparilla Root, Saw Palmetto, Saw Palmetto Berry, Schisandra Berries, Schisandra, Scullcap Herb, Shavegrass Herb, Sheep Sorrel, Shepard's Purse Herb, Shitake Mushroom, Slippery Elm Bark, Sown Orange, Soybean, Stevia Rebaudiana, St. John's Wort, Tetrandrine, Turmeric, Usnea Lichen, Uva Ursi, Uva Ursi Leaf, Valerian Root, White Willow Bark, Wild Yam Root, Yellow Dock Root, Yohimbe Bark, Yucca Root, and combinations thereof.

4. A process of creating agglomerated particles containing an herbal extract comprising:
   a) providing an herbal extract suitable for spray drying; and
   b) combining the herbal extract with dry silicified microcrystalline cellulose in a spray dryer and
   c) spray drying to form agglomerated particles.

5. The process of claim 4, wherein the herbal extract is hygroscopic.

6. A method of manufacturing agglomerated particles containing a herbal extract comprising combining a wetted herbal extract with dry silicified microcrystalline cellulose in a spray dryer and spray drying to form agglomerated particles.

7. The method of claim 6, wherein said silicified microcrystalline cellulose comprises excipient particles comprising a particulate agglomerate of microcrystalline cellulose coprocessed with from about 0.1% to about 20% by weight silicon dioxide, the microcrystalline cellulose and silicon dioxide being in intimate association with each other and said silicon dioxide being integrated with or partially coating said microcrystalline cellulose, said silicon dioxide portion of said agglomerate being derived from a silicon dioxide having an average primary particle size from about 1 nm to about 100 µm.

8. The method of claim 6, wherein said silicon dioxide is derived from a silicon dioxide having an average primary particle size from about 5 nm to about 40 µm.

9. The method of claim 6, wherein said silicon dioxide is derived from colloidal silicon dioxide.

10. The method of claim 6, wherein said silicon dioxide is from about 0.5% to about 10% by weight, based on the weight of said microcrystalline cellulose.

11. The method of claim 6, wherein said excipient particles have an average particle size of from about 10 µm to about 500 µm.

12. The method of claim 6, wherein said silicon dioxide is derived from a silicon dioxide having a surface area from about 175 $m^2/g$ to about 350 $m^2/g$.

13. The method of claim 11, wherein said excipient has a bulk density from about 0.35 g/ml to about 0.55 g/ml.

* * * * *